United States Patent
Lee et al.

(10) Patent No.: US 9,662,347 B2
(45) Date of Patent: May 30, 2017

(54) METHOD FOR INHIBITING THE INDUCTION OF CELL DEATH BY INHIBITING THE SYNTHESIS OR SECRETION OF AGE-ALBUMIN IN CELLS OF THE MONONUCLEAR PHAGOCYTE SYSTEM

(75) Inventors: Bong Hee Lee, Jeju-do (KR); Kyung Hee Byun, Jeju-do (KR)

(73) Assignee: Gachon University of Industry-Academic Cooperation Foundation, Seongnam-si (KR)

( * ) Notice: Subject to any disclaimer, the term of this patent is extended or adjusted under 35 U.S.C. 154(b) by 47 days.

(21) Appl. No.: 13/697,332

(22) PCT Filed: Apr. 28, 2011

(86) PCT No.: PCT/KR2011/003147
§ 371 (c)(1),
(2), (4) Date: Jan. 24, 2013

(87) PCT Pub. No.: WO2011/142545
PCT Pub. Date: Nov. 17, 2011

(65) Prior Publication Data
US 2013/0131006 A1    May 23, 2013

(30) Foreign Application Priority Data

May 11, 2010    (KR) .................. 10-2010-0043783
Apr. 28, 2011    (KR) .................. 10-2011-0039984

(51) Int. Cl.
*A61K 31/7076* (2006.01)
*A61K 31/13* (2006.01)
(Continued)

(52) U.S. Cl.
CPC .......... *A61K 31/7076* (2013.01); *A61K 31/13* (2013.01); *A61K 31/137* (2013.01);
(Continued)

(58) Field of Classification Search
CPC .... A61K 31/13; A61K 31/137; A61K 31/165; A61K 31/196; A61K 31/197;
(Continued)

(56) References Cited

U.S. PATENT DOCUMENTS 5,264,356 A † 11/1993 Rohrschneider
6,133,299 A † 10/2000 Taylor
(Continued)

FOREIGN PATENT DOCUMENTS

EP    0607776    † 12/1998
EP    1356812    † 5/2009
(Continued)

OTHER PUBLICATIONS

Belanoff et al. (Journal of Molecular Neuroscience, 2002, vol. 19, pp. 201-206).*
(Continued)

*Primary Examiner* — Savitha Rao
(74) *Attorney, Agent, or Firm* — Seed IP Law Group LLP

(57) ABSTRACT

The present invention relates to a method for inhibiting the induction of cell death by inhibiting the synthesis or secretion of AGE-albumin in cells of the mononuclear phagocyte system, to an AGE-albumin synthesis inhibitor, and to a pharmaceutical composition comprising the AGE-albumin synthesis inhibitor for preventing or treating degenerative disease and autoimmune disease. The AGE-albumin of the present invention is synthesized and secreted in human microglia or human macrophages in an Alzheimer's model, stroke model, Parkinson's disease model and rheumatoid arthritis model. The AGE-albumin synthesis and secretion are caused by oxidative stress. The expression of RAGE increases in first-order human neurons or cartilage cells to which AGE-albumin is administered, whereupon a MAPK signaling pathway is activated and the expression of Bax
(Continued)

increases to induce an increase in calcium in mitochondria, thus finally inducing cell death. Therefore, the AGE-albumin synthesis inhibitor of the present invention can be valuably used in the diagnosis or treatment of degenerative diseases or autoimmune diseases such as Alzheimer's disease, strokes, Parkinson's disease, amyotrophic lateral sclerosis, rheumatoid arthritis, diabetic retinopathy, AIDS, aging, pulmonary fibrosis, spinal cord injuries, etc.

6 Claims, 38 Drawing Sheets

(51) Int. Cl.
| | | |
|---|---|---|
| A61K 31/197 | (2006.01) | |
| A61K 31/221 | (2006.01) | |
| A61K 31/4168 | (2006.01) | |
| A61K 31/196 | (2006.01) | |
| A61K 31/225 | (2006.01) | |
| A61K 31/473 | (2006.01) | |
| A61K 31/4745 | (2006.01) | |
| A61K 31/519 | (2006.01) | |
| A61K 31/545 | (2006.01) | |
| A61K 31/546 | (2006.01) | |
| A61K 31/56 | (2006.01) | |
| A61K 31/663 | (2006.01) | |
| A61K 31/137 | (2006.01) | |
| A61K 31/165 | (2006.01) | |
| A61K 31/40 | (2006.01) | |
| A61K 31/445 | (2006.01) | |
| A61K 31/4525 | (2006.01) | |
| A61K 31/713 | (2006.01) | |

(52) U.S. Cl.
CPC .......... *A61K 31/165* (2013.01); *A61K 31/196* (2013.01); *A61K 31/197* (2013.01); *A61K 31/221* (2013.01); *A61K 31/225* (2013.01); *A61K 31/40* (2013.01); *A61K 31/4168* (2013.01); *A61K 31/445* (2013.01); *A61K 31/4525* (2013.01); *A61K 31/473* (2013.01); *A61K 31/4745* (2013.01); *A61K 31/519* (2013.01); *A61K 31/545* (2013.01); *A61K 31/546* (2013.01); *A61K 31/56* (2013.01); *A61K 31/663* (2013.01); *A61K 31/713* (2013.01)

(58) Field of Classification Search
CPC .... A61K 31/221; A61K 31/225; A61K 31/40; A61K 31/4168; A61K 31/445; A61K 31/4525; A61K 31/473; A61K 31/4745; A61K 31/519
See application file for complete search history.

(56) References Cited

U.S. PATENT DOCUMENTS

| | | | |
|---|---|---|---|
| 7,354,574 B2 † | 4/2008 | Peyman | |
| 2003/0013692 A1 † | 1/2003 | Gullans | |
| 2003/0060487 A1 * | 3/2003 | Bamdad | A61K 31/137 514/326 |
| 2004/0063742 A1 † | 4/2004 | Peters | |
| 2004/0082644 A1 † | 4/2004 | Korsten | |
| 2005/0026919 A1 † | 2/2005 | Stephenson | |
| 2005/0090554 A1 † | 4/2005 | Devane | |
| 2006/0252788 A1 * | 11/2006 | Went et al. | 514/294 |
| 2007/0203239 A1 † | 8/2007 | Gehenne | |
| 2008/0044390 A1 * | 2/2008 | Jin | A61K 31/155 424/93.7 |
| 2009/0176740 A1 † | 7/2009 | Phillips, II | |
| 2010/0004156 A1 † | 1/2010 | Kaushal | |
| 2010/0143346 A1 † | 6/2010 | Richards | |

FOREIGN PATENT DOCUMENTS

| | | | | |
|---|---|---|---|---|
| EP | 1611238 | † | 6/2009 | |
| WO | 9815267 | † | 4/1998 | |
| WO | 9961014 | † | 12/1999 | |
| WO | 2004012762 | † | 2/2004 | |
| WO | 2005074535 | † | 8/2005 | |
| WO | 2006091887 | † | 8/2006 | |
| WO | WO2006119329 | * | 11/2006 | ............ A61K 31/13 |
| WO | 2009019473 | † | 2/2009 | |
| WO | 2009051922 | † | 4/2009 | |
| WO | 2010027266 | † | 3/2010 | |
| WO | 2010054336 | † | 5/2010 | |

OTHER PUBLICATIONS

Rahbar et al., "Novel inhibitors of advanced glycation endproducts," *Archives of Biochemistry and Biophysics* 419:63-79, 2003.
Ahn et al., "Human Microglial Cells Synthesize Albumin in Brain," *Public Library of Science ONE* 3(7):e2829, Jul. 2008, 6 pages.
Cameron et al., "Inhibitors of Advanced Glycation End Product Formation and Neurovascular Dysfunction in Experimental Diabetes," *Annals of the New York Academy of Sciences* 1043:784-792, 2005.
Dukic-Stefanovic et al., "AGES in brain ageing: AGE-inhibitors as neuroprotective and anti-dementia drugs?," *Biogerontology* 2:19-34, 2001.
Strand et al., "Treatment of Active Rheumatoid Arthritis With Leflunomide Compared With Placebo and Methotrexate," *Archives of Internal Medicine* 159:2542-2550, Nov. 22, 1999.
Symmetrel® (Amantadine Hydrochloride, USP) Tablets and Syrup, ENDO Pharmaceuticals Inc., pp. 1-15, Jan. 2009.
Young et al Paroxetine Prevents Loss of Nigrostriatal Dopaminergic Neurons by Inhibiting Brain Inflammation and Oxidative Stress in an Experimental Model of Parkinsons Disease pp. 1230-1237 Jun. 21, 2010 The journal of Immunology US.†

* cited by examiner
† cited by third party

METHOD FOR INHIBITING THE INDUCTION OF CELL DEATH BY INHIBITING THE SYNTHESIS OR SECRETION OF AGE-ALBUMIN IN CELLS OF THE MONONUCLEAR PHAGOCYTE SYSTEM

TECHNICAL FIELD

The present invention relates to a method for inhibiting AGE-albumin-mediated cell death induction in cells of the mononuclear phagocyte system, an inhibitor of AGE-albumin synthesis, and a pharmaceutical composition for the prophylaxis or therapy of degenerative diseases and autoimmune diseases.

BACKGROUND ART

Recent studies have revealed that the pathogenesis of various diseases is essentially due to abnormal functions in the apoptosis signal transduction system. Apoptosis modulating therapy is designed to control cell growth and death by inducing or suppressing apoptosis, with the aim of fundamentally reversing diseases by converting abnormal cells to normal ones as well as halting the progression of diseases by the apoptosis of abnormal cells. Hence, a technology controlling reversibly cell survival-death accounts for the next generation of core technology for apoptosis modulating therapy.

Apoptosis modulating therapy, which is now competitively being developed across the world, can find applications in the treatment of various diseases including leukemia, cancer, AIDS, and senile and degenerative diseases such as Alzheimer's disease, Parkinson's disease, and aging. However, apoptosis modulating therapy is arising as a fundamental technique applicable to a wider spectrum of diseases as abnormal functions of the apoptosis signal transduction system are revealed to account for the onset of most diseases.

Designed to either suppress the pathological uncontrollable growth of cells such as cancerous cells or to prevent normal cells from undergoing excessive cell death as in degenerative diseases such as Alzheimer's disease or Parkinson's disease, apoptosis modulating therapy can be used in the therapy of diseases. For cancer, for example, conventional chemotherapy, characterized by causing necrosis over a wide range of cells, not only kills pathological cells, but also exhibits cytotoxicity to normal cells with the concomitant induction of excessive inflammation, as cytotoxic enzymes (e.g., lysozymes) are released upon the lysis of the pathological cells. By contrast, apoptosis modulating therapy induces pathological cells to undergo apoptosis or strongly suppresses the growth of pathological cells without the inflammatory side effects caused by the necrosis of cancer cells. When cells are under the potent effect of growth inhibition, cancer cells are more greatly restrained from growing than are normal cells because of the greater proliferative activity of cancer cells. If this inhibitory effect is maximized to induce apoptosis, various cytotoxic intracellular factors are for the most part digested by caspase during apoptosis to lose their functions while being surrounded by apoptotic bodies and subsequently phagocytosed by macrophages. During phagocytosis, the cytotoxic factors are neither released extracellularly nor exert cytotoxicity on surrounding cells.

Programmed cell death (apoptosis) is active death of a cell requiring energy, with the accompaniment of characteristic morphological changes. Given an apoptotic signal, a cell is triggered to destroy itself and commits suicide. In this phase, the cell undergoes biochemical events which lead to morphological changes. Once apoptosis proceeds, cells shrink and separate from adjacent cells, showing membrane blebbing, chromatic condensation, and chromosomal DNA fragmentation and forming apoptotic bodies that phagocytic cells are able to engulf and quickly remove before the contents of the cell can spill out onto surrounding cells and cause damage. Apoptosis is a complex intracellular process. Although not easily determined, apoptosis may be achieved via various downstream pathways once it is triggered. Caspases, which are aspartic acid specific cysteine proteases, are responsible for most morphological changes which take place during apoptosis.

Albumin is a multifunctional protein which is most abundantly found in blood plasma. This plasma protein is produced mainly in the liver and is a major component of most extracellular fluids including interstitial fluid, lymph, and cerebrospinal fluid. Since a reduced level of albumins may lead to hepatic dysfunction and malnutrition, albumin has been extensively used for critical conditions including vascular collapse in serious patients or hepatic cirrhosis patients in clinics. In addition, recent research has suggested that albumin specifically binds to low-molecular weight molecules that might be important diagnostic or prognostic indicators of diseases. For example, albumin is reported to enter the brain across the blood-brain barrier by molecular diffusion and also to be implicated in Alzheimer's disease because it can specifically bind to and transport amyloid beta 1-42 (Aβ1-42). The present inventors reported in 2008 the finding that albumin can be synthesized in microglial cells, a kind of cells of the mononuclear phagocyte system, in the brain and that the synthesis and extracellular secretion of albumin from microglial cells increases upon microglial activation with Aβ1-42 [Ahn S-M, Byun K, Cho K, Kim J Y, Yoo J S, et al. (2008) Human Microglial Cells Synthesize Albumin in Brain. PLoS ONE 3(7): e2829].

Advanced glycation end-products (AGEs) are complex products which are incessantly produced inside the body mainly by reactions between carbohydrates and free amino acids. AGEs are chemically very unstable and reactive and are known as potent molecules that promote neuronal cell death. AGEs are also reported to be found in increased levels in the brain of senile persons or animals, and to exert influences on all cells and biological molecules, causing senescence and senescence-related chronic diseases. That is, AGEs are involved in senescence, Alzheimer's disease, renal disease, diabetes mellitus, diabetic vascular complications, diabetic retinopathy and diabetic neuropathy, due to enhancing vascular permeability, suppressing vasodilation via nitrogen oxide interference, and increasing LDL oxidation, the release of various cytokines from phagocytes or endothelial cells, and oxidative stress.

Since AGEs are found, as described above, at an elevated level in the brain of senile persons or animals, many scientists have suggested that AGEs might have influences on neurodegenerative diseases such as Alzheimer's disease by promoting neuronal cell death. In spite of extensive research results, the precise synthesis mechanism or main secretion places of AGEs still remain unknown.

Hence, the discovery of the precise synthesis mechanism and origin of AGEs may be helpful in finding a method for inhibiting the induction of cell death, thus contributing a clue to the etiology of various diseases. There is therefore a need for researching the precise synthesis mechanism of AGEs by which the pathology of various diseases can be revealed.

DISCLOSURE

Technical Problem

Leading to the present invention, intensive and thorough research into the main synthesis mechanism of AGEs, conducted by the present inventors, aiming to develop a method for inhibiting the induction of cell death, resulted in the finding that AGE-albumin is synthesized in human microglial cells or phagocytes in Alzheimer's disease, stroke, Parkinson's disease and rheumatoid arthritis models and secreted into the extracellular space, with a drastic increase in AGE-albumin level with oxidative stress, and induces the aggregation of Aβ1-42 in the brain tissues of Aβ1-42-treated rats and patients with Alzheimer's disease, and that the AGE-albumin synthesized and released from human microglial cells or phagocytes upregulates receptor of AGE (RAGE) in primary neurons or chondrocytes, which subsequently brings about activation in the MAPK signaling pathway, an increase in Bax level, and augmentation in mitochondrial calcium influx, thus triggering apoptosis.

Technical Solution

It is therefore an object of the present invention to provide a method for inhibiting AGE-albumin-induced cell death in cells of the mononuclear phagocyte system by inhibiting synthesis or secretion of AGE-albumin.

It is another object of the present invention to provide an inhibitor of AGE-albumin synthesis comprising a compound inhibitory of the synthesis of AGE-albumin.

It is a further object of the present invention to provide a pharmaceutical composition for the prevention or treatment of neurodegenerative diseases and autoimmune diseases, comprising an inhibitor of AGE-albumin synthesis as an active ingredient.

It is a still further object of the present invention to provide a method for preventing or treating a neurodegenerative disease and an autoimmune disease, comprising administering a therapeutically effective amount of an inhibitor of AGE-albumin synthesis to a subject in need thereof.

Advantageous Effects

In the present invention, AGE-albumin is reported to be synthesized and secreted in human microglical cells or macrophages in models of Alzheimer's disease, stroke, Parkinson's disease, and rheumatoid arthritis, and the synthesis and secretion of AGE-albumin is promoted by oxidative stress. When exposed to AGE-albumin, primary human neurons or chondrocytes increase in RAGE level, which triggers a complex pathologic cascade including the MAPK signaling transduction pathway, Bax activation, and mitochondrial calcium influx, leading to cell death. Therefore, an inhibitor of AGE-albumin synthesis in accordance with the present invention may be effectively used for the diagnosis or treatment of neurodegenerative and autoimmune diseases including Alzheimer's disease, stroke, Parkinson's disease, Lou Gehrig's disease, as well as rheumatoid arthritis, diabetic retinopathy, AIDS, senescence, pulmonary fibrosis, and spinal cord injuries.

BEST MODE

Figure 1:
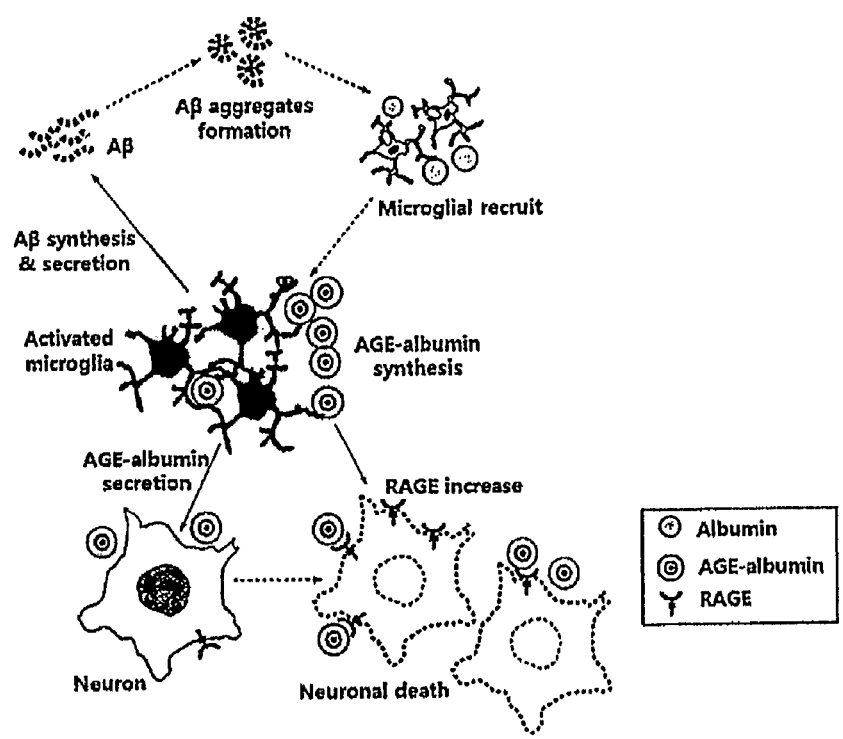
FIG. 1 is a schematic view illustrating the method of the present invention by which the synthesis or secretion of AGE-albumin in cells of the mononuclear phagocyte system is suppressed to inhibit the induction of cell death in surrounding cells.

In accordance with an aspect thereof, the present invention provides a method for inhibiting AGE-albumin-induced cell death in cells of the mononuclear phagocyte system by inhibiting the synthesis or secretion of AGE-albumin.

In accordance with another aspect thereof, the present invention provides an inhibitor of AGE-albumin synthesis comprising a compound inhibitory of the synthesis of AGE-albumin.

In accordance with a further aspect thereof, the present invention provides a pharmaceutical composition for the prevention or treatment of neurodegenerative diseases and autoimmune diseases, comprising an inhibitor of AGE-albumin synthesis as an active ingredient.

In accordance with a further aspect thereof, the present invention provides a method for preventing or treating a neurodegenerative disease and an autoimmune disease, comprising administering a therapeutically effective amount of an inhibitor of AGE-albumin synthesis to a subject in need thereof.

Below, a detailed description will be given of the present invention.

In the method for inhibiting cell death in accordance with the present invention, the synthesis or secretion of AGE-albumin in cells of the mononuclear phagocyte system is inhibited to inhibit the induction of the cell death of cells of the mononuclear phagocyte system and neighboring cells from undergoing cell death.

Cell death is divided into necrosis and apoptosis. Necrosis is a form of cell injury, caused by a stimulus such as a burn, contusion, toxin, etc., which results in the premature death of cells in living tissue, and thus is called accidental cell death. In necrosis pathways, cells swell with an influx of water and then proceed to blebbing. In past years, all forms of the death of cells were considered to be necrosis. From about 30 years ago, factors that cause spontaneous cell death have become known. Active cell death regulated by genes is apoptosis. Necrosis occurs in a disorderly fashion over a long period of time while apoptosis takes place in an ordered pattern within a short time. Apoptosis starts with cell shrinkage. Thus, the apoptotic cell is detached from adjacent cells while nuclear DNA is regularly degraded into fragments. Finally, the whole cell breaks apart into several vesicles called apoptotic bodies, which are then phagocytosed, and thus cell death is completed. Apoptosis accounts for morphogenesis in a developing embryo, and the renewal of normal cells or the removal of abnormal cells in an adult body. Programmed cell death (PCD) is death of a cell in any form, mediated by an intracellular program during the development and differentiation of tissues in animals and plants. In any phase of the embryogenesis, a fatal gene is activated to order a cell to commit suicide. For example, the differentiation of fingers and toes in a developing human embryo occurs because cells between the fingers or toes apoptose; the result is that the digits are separate. Degenerative diseases are known to be accompanied by the two forms of cells.

Cells of the mononuclear phagocyte system in the present invention are preferably activated by, but not limited to, amyloid beta 1-42 (Aβ1-42), HMGB1, rotenone, 6-hydroxy-dopamine (6-OHDA), or β2-microglobulin.

The cells that are induced to undergo apoptosis in accordance with the present invention are those surrounding the cells of the mononuclear phagocyte system. Preferable among them are neurons, chondrocytes, pneumocytes and hepatocytes.

Suppressing the synthesis and secretion of AGE-albumin may be implemented with an inhibitor selected from the group consisting of an albumin siRNA, an albumin antibody, an AGE antibody, an AGE-albumin antibody, and an inhibitor of AGE-albumin.

Examples of the cells of the mononuclear phagocyte system include brain microglial cells, blood monocytes, alveolar macrophages (type II pneumocytes, dust cells), peritoneal macrophages, granuloma macrophages in inflammation regions, splenic macrophages, Kupffer's cells of the liver, synovial A cells, adventitial cells, macrophages within lymph nodes, and epidermal Langerhans cells, but are not limited thereto.

FIG. 1 is a conceptual diagram illustrating the method of the present invention by which the synthesis or secretion of AGE-albumin in cells of the mononuclear phagocyte system is suppressed to inhibit the induction of cell death in surrounding cells.

In human microglial cells, macrophages, brain tissues or cartilages of Alzheimer's disease, stroke, Parkinson's disease, and rheumatoid arthritis models, albumin and AGE were observed to be stained at the same positions and were widely distributed, with a remarkable elevation of AGE-albumin in expression level and density compared to normal brain tissues or cartilages. In addition, the microglial marker Iba1 was co-localized with AGE-albumin. Accordingly, most AGE-albumin is predicted to be synthesized in human microglial cells or macrophages.

Moreover, the expression level of AGE-albumin increases in human microglial cells, macrophages, brain tissues or cartilages of Alzheimer's disease, stroke, Parkinson's disease, and rheumatoid arthritis models following exposure to amyloid beta 1-42 (Aβ1-42), HMGB1, rotenone, 6-hydroxy-dopamine, or β2-microglobulin. Furthermore, the expression level of AGE-albumin in human microglial cells of Alzheimer's disease, stroke, Parkinson's disease, and rheumatoid arthritis models increases with an increase in hydrogen peroxide ($H_2O_2$) exposure, whereas it drastically decreases upon exposure to the antioxidant ascorbic acid. In addition, oxidative stress induces human microglial cells to accumulate Aβ1-42 therein, which leads to the synthesis of AGE-albumin. This indicates that oxidative stress is, at least in part, responsible for the synthesis and secretion of AGE-albumin in human microglial cells.

When exposed to AGE-albumin, primary human neurons or chondrocytes increase in RAGE level, which triggers a complex pathologic cascade including the MAPK signaling transduction pathway, Bax activation, and mitochondrial calcium influx, leading to cell death. However, cell death is observed at a reduced rate when exposure to both AGE-albumin and soluble RAGE (sRAGE), indicating that sRAGE has a protective effect on cells against cell death.

As described hitherto, AGE-albumin is synthesized or secreted by human microglial cells or macrophages of Alzheimer's disease, stroke, Parkinson's disease, and rheumatoid arthritis models, with a drastic increase in AGE-albumin level with oxidative stress, and upregulates RAGE (receptor of AGE) in primary neurons or chondrocytes, which subsequently brings about activation of the MAPK signaling pathway, an increase in Bax level, and augmentation in mitochondrial calcium influx, thus leading to apoptosis.

In the present invention, 1,280 LOPAC (Sigma) compounds were screened for inhibitory activity against the synthesis of AGE-albumin in human microglial cells or macrophages of Alzheimer's disease, stroke, Parkinson's disease, and rheumatoid arthritis models, and 42 compounds were identified as having inhibitory activity similar to that of the control. Therefore, the identified inhibitors of AGE-albumin synthesis can be effectively used for the diagnosis or treatment of neurodegenerative and autoimmune diseases including Alzheimer's disease, stroke, Parkinson's disease, Lou Gehrig's disease, and rheumatoid arthritis, diabetic retinopathy, AIDS, senescence, pulmonary fibrosis, and spinal cord injuries.

The pharmaceutical composition of the present invention may comprise at least one active ingredient known for the prevention or treatment of neurodegenerative and autoimmune diseases, in addition to the inhibitor of AGE-albumin.

In addition to the active ingredients, the pharmaceutical composition may further comprise a pharmaceutically acceptable carrier. Examples of the pharmaceutically acceptable carrier include saline, sterile water, Ringer's solution, buffered saline, dextrose solution, maltodextrin solution, glycerol, ethanol, etc. Optionally, ordinary additives, such as antioxidants, buffers, bacteriostatic agents, etc., may be added to the composition. For the preparation of dosage forms including injections, such as aqueous solutions, suspensions and emulsions, pills, capsules, granules and tablets, the active ingredients may be admixed with a diluent, a dispersant, a surfactant, a binder and/or a lubricant. Reference may be made to literature (Remington's Pharmaceutical Science (latest edition), Mack Publishing Company, Easton Pa.) regarding the formulation of the pharmaceutical composition into suitable dosage forms.

The composition of the present invention may be administered via oral routes or parenteral routes (e.g., intravenous, subcutaneous, intraperitoneal, topical, etc.). The effective dosage of the inhibitor in accordance with the present invention depends on various factors, including the patient's weight, age, gender, state of health, diet, the time of administration, route of administration, excretion rate, severity of diseases, etc. In general, the inhibitor of AGE-albumin synthesis may be administered in a single dose, and preferably in multiple doses per day at a daily dose ranging from 0.1 to 10 mg/day, and preferably from 0.5 to 2 mg/kg.

For the effective prevention and treatment of neurodegenerative and autoimmune diseases, the composition according to the present invention may be used alone or in combination with surgical operation, hormonal therapy, a drug, and/or biological response controllers.

Also, the present invention addresses a method for the prevention or treatment of neurodegenerative diseases and autoimmune diseases comprising administering an inhibitor of AGE-albumin synthesis at a therapeutically effective dose to a subject in need thereof.

Mode for Invention

A better understanding of the present invention may be obtained through the following examples which are set forth to illustrate, but are not to be construed as limiting the present invention.

EXAMPLE 1

Distribution and Expression Position of AGE-Albumin in Brain Tissue of Alzheimer's Disease Patient The following experiment was carried out to examine the distribution and expression position of AGE-albumin in microglial cells of normal or Alzheimer's disease models, brain tissues of normal persons or Alzheimer's disease patients, and brain tissues of normal or Alzheimer's disease animal models.

1. Cell Culture

For in vitro studies, the immortalized human microglial cell line HMO6 was used. HMO6 cells were grown in Dulbecco's modified Eagle's medium (DMEM, Gibco) containing a high glucose concentration, supplemented with 10% heat-inactivated fetal bovine serum (FBS, Gibco) and 20 mg/mL gentamycin (Sigma-Aldrich). These cells were maintained at 37° C. under 5% $CO_2$. HMO6 cells were exposed to Aβ1-42 (Sigma-Aldrich) at concentrations from 0 to 400 nM. HMO6 cells were then harvested 6 hrs after Aβ1-42 treatment for further analysis.

2. Immunocytochemistry (ICC)

Cells were grown on Lab-Tek II slide chambers (Nunc), rinsed with PBS, fixed in methanol for 15 min, and rinsed again with PBS. The fixed cells on slide chambers were incubated overnight at 4° C. with the following primary antibodies: rabbit anti-AGE antibody (1:200, Abcam), mouse anti-human-albumin antibody (1:200, R&D System), anti-BACE antibody (1:50, Santa Cruz), anti-ADAM10 antibody (1:200, R&D System), anti-APP antibody (1:200, Chemicon), anti-RAGE antibody (1:50, Santa Cruz), or anti-mitochondria antibody (1:50, Abcam). After overnight incubation, the primary antibodies were washed three times with PBS and the slides were incubated for 1 hr at room temperature with one of the following secondary antibodies: Alexa Fluor 633 anti-mouse IgG (1:500, Invitrogen), Alexa Fluor 488 anti-rabbit IgG (1:500, Invitrogen), and Alexa Fluor 555 anti-goat IgG (1:500, Invitrogen). After washing the secondary antibodies with PBS three times at regular intervals of 10 min, coverslips were mounted onto glass slides using the Vectashield mounting medium (Vector Laboratories), and examined under a laser confocal fluorescence microscope (LSM-710, Carl Zeiss).

3. Immunohistochemistry (IHC)

Immunohistochemistry was conducted on murine brain tissues from normal or Alzheimer's disease rats, and human brain tissues from normal adults and Alzheimer's disease individuals [S. M. Ahn et al., PLoS ONE 3, e2829 (2008)]. The human brain tissues from normal adults and Alzheimer's disease individuals were obtained from the Brain Bank of Seoul National University Hospital and the Brain Bank of Niigata University Hospital. Brain tissues were fixed in 4% paraformaldehyde in a 0.1 M neutral phosphate buffer, cryopreserved overnight in a 30% sucrose solution, and then sectioned on a cryostat (Leica CM 1900) at a 10 μm thickness. Paraffin-embedded brain tissues were cut into 4 μm-thick sections, deparaffinized with xylene, and rehydrated with a series of graded ethanol. Normal goat serum (10%) was used to block non-specific protein binding. The tissue sections were incubated overnight at 4° C. with the following primary antibodies: rabbit anti-AGE antibody (1:200, Abcam), mouse anti-human albumin antibody (1:200, R&D System), goat anti-Iba1 antibody (1:500, Abcam), anti-MBP antibody (1:200, Chemicon), anti-Olig2 antibody (1:100, R&D System), anti-NeuroD1 antibody (1:200, R&D System), anti-BACE antibody (1:50, Santa Cruz), anti-ADAM10 antibody (1:200, R&D System), anti-APP antibody (1:200, Chemicon), anti-JNK antibody (1:200, Cell Signaling), anti-p-JNK antibody (1:200, Cell Signaling), and anti-Bax antibody (1:50, Santa Cruz). Then, the tissue sections were washed three times with PBS before incubation for 1 hr at room temperature with one of the secondary antibodies: Alexa Fluor 633 anti-mouse IgG (1:500, Invitrogen), Alexa Fluor 488 anti-rabbit IgG (1:500, Invitrogen), and Alexa Fluor 555 anti-goat IgG (1:500, Invitrogen). After washing the secondary antibodies three times with PBS, coverslips were mounted onto glass slides using the Vectashield mounting medium (Vector Laboratories), and observed under a laser confocal fluorescence microscope (LSM-710, Carl Zeiss). The distribution, and expression position of AGE (red), albumin (green), and DAPI (4',6-diamidino-2-phenylindole) (blue), in microglial cells and murine brain tissues before and after Aβ1-42 treatment and in human brain tissues from normal adults and Alzheimer's disease patients were examined by laser confocal fluorescence microscopy. Also, the density of AGE-albumin was measured. Other staining methods were the same as described in the immunocytochemistry (ICC).

Figure 2:
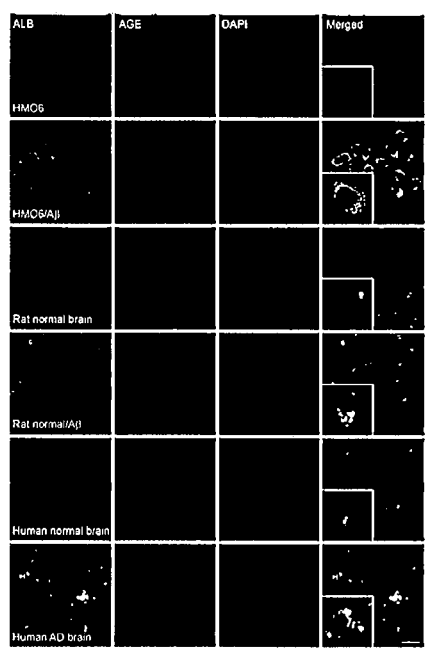
FIG. 2 shows laser confocal fluorescence microscopic images taken from human microglial cells and murine brain tissues before and after Aβ1-42 treatment and from brain tissues from normal adults and Alzheimer's disease patients after immunostaining with antibodies, showing the distribution and expression positions of AGE-albumin.
Figure 3:
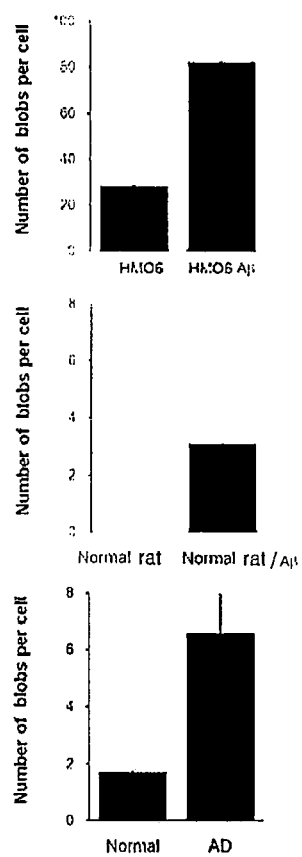
FIG. 3 shows graphs in which densities of AGE-albumin in human microglial cells and murine brain tissues before and after Aβ1-42 treatment and from brain tissues from normal adults and Alzheimer's disease patients are represented.

Laser confocal fluorescence microscopic images taken from human microglial cells and murine brain tissues before and after Aβ1-42 treatment and from brain tissues from normal adults and Alzheimer's disease patients after immunostaining are given in FIG. 2, showing the distribution and expression positions of AGE-albumin, and the density of AGE-albumin is represented in FIG. 3.

As can be seen in FIG. 2, albumin (green) and AGE (red) are stained at the same positions in human microglial cells and rat brain tissues before and after Aβ1-42 treatment and in brain tissues from normal adults and Alzheimer's disease patients. The albumins were, for the most part, glycosylated. In addition, the human microglial cells and rat brain tissue (cerebral cortex) after exposure to Aβ1-42 were observed to have a wide distribution of albumin and AGE, with a remarkable elevation in the expression level of AGE-albumin.

In addition, as shown in FIG. 3, the densities of AGE-albumin in microglial cells and rat brain tissues after Aβ1-42 treatment and in human brain tissues of Alzheimer's disease patients were remarkably higher than those in microglial cells and rat brain tissues before Aβ1-42 treatment and in human brain tissues of normal adults, respectively. Particularly, the level of AGE-albumin in brain tissues of Alzheimer's disease patients was 3.4 times as high as that in brain tissues of normal adults.

EXAMPLE 2

Confirmation of the Distribution and Expression Position of AGE-Albumin in Brain Tissue of Alzheimer's Disease Patient After detecting elevated levels of AGE-albumin in both Aβ1-42-treated rat brain tissues and human brain tissues of Alzheimer's disease patients, immunohistochemistry was conducted on brain tissues of Alzheimer's disease patients in order to confirm the distribution and expression position of AGE-albumin. The brain tissues of Alzheimer's disease patients were immunostained for AGE (red), albumin (green), the microglial cell marker Iba1 (blue), the astrocyte cell marker MBP (blue), the oligodendrocyte cell marker Olig2 (blue), the neuronal cell marker NeuroD (blue), and AGE-albumin, followed by laser confocal fluorescence microscopy to examine distributions and expression positions of albumin and AGE.

Figure 4:
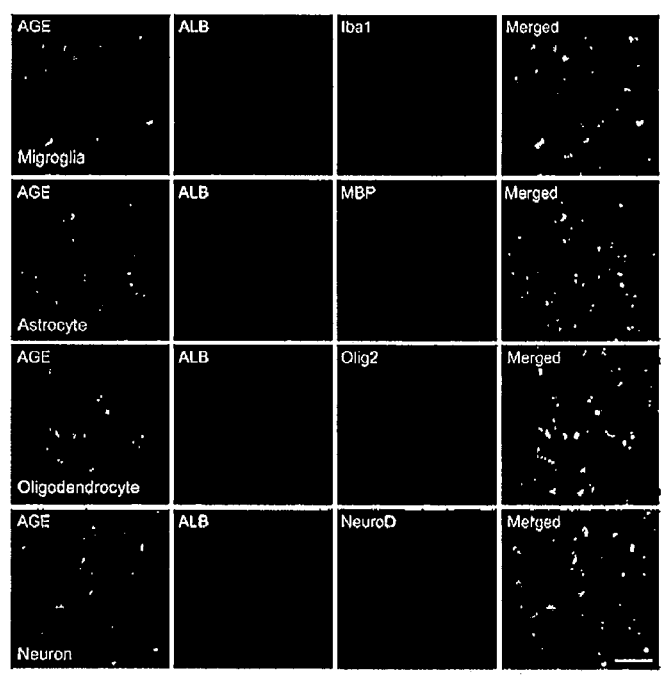
FIG. 4 shows laser confocal fluorescence microscopic images taken from brain tissues of Alzheimer's disease patients after immunostaining for AGE (red), albumin (green), the microglial cell marker Iba1 (blue), the astrocyte cell marker MBP (blue), the oligodendrocyte cell marker Olig2 (blue), the neuronal cell marker NeuroD (blue), and AGE-albumin, showing distributions and expression positions of albumin and AGE.

The results are given in FIG. 4.

As can be seen in FIG. 4, the microglial cell marker Iba1 was co-localized with AGE-albumin in the human brain tissue of Alzheimer's disease patients while almost no co-localization of albumin with the non-microglial cell markers MBP for astrocyte cells, Olig2 for oligodendrocyte cells, and NeuroD for neuronal cells were observed. Therefore, most AGE-albumin is anticipated to be synthesized in microglial cells.

EXAMPLE 3

Synthesis and Secretion of AGE-Albumin in Human Microglial Cell

To examine whether human microglial cells synthesize and secrete AGE-albumin, expression levels of AGE-albumin were measured using a co-immunoprecipitation method and ELISA.

1. Co-Immunoprecipitation

Whole human microglial cell lysates prepared before and after Aβ 1-42 treatment were subjected to immunoblotting analysis. In this regard, whole cell lysates from human microglial cells before and after treatment with 0~400 nM Aβ 1-42 were prepared with a RIPA (radioimmunoprecipitation assay) buffer containing 1 M Tris (pH 7.5), 5 M NaCl, 10% NP-40, 10% deoxycholate and a protease inhibitor cocktail (Calbiochem). All cell lysates (1 mg protein) were incubated overnight at 4° C. with 5 mg of anti-AGE (Abcam)-conjugated sepharose beads in 500 mL of PBS. The sepharose beads were precipitated by centrifugation at 14,000 rpm for 5 min, and washed three times with 1 mL of washing buffer containing 50 mM Tris-Cl and 500 mM NaCl (pH 8.0). The IgG-bound antigen-antibody complex was resolved on a 4-12% polyacrylamide gel (Invitrogen), followed by immunoblot analysis with the respective antibodies (1:1000, Abcam).

Figure 5:
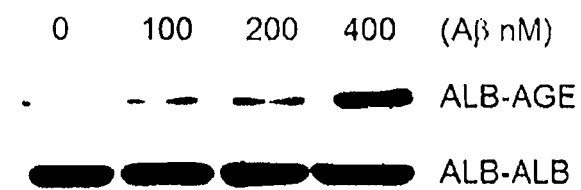
FIG. 5 shows expression levels of AGE-albumin in human microglial cells as measured by co-immunoprecipitation.

The results are given in FIG. 5.

As seen in FIG. 5, the expression level of AGE-albumin in human microglial cells was increased with an increase in the concentration of Aβ1-42 to which the cells had been exposed.

2. Intracellular and Extracellular Levels of AGE-Albumin (ELISA)

After removal of already synthesized albumin by use of an anti-albumin antibody, intracellular and extracellular (secreted into culture media) levels of AGE-albumin were measured using ELISA. For this, human microglial cells were treated with 0-400 nM Aβ1-42, after which the culture media (0.1 mg protein) were harvested. Separately, the cells were lyzed to prepare cell lysates (0.5 mg protein). AGE-albumin was quantitated using a rabbit anti-AGE antibody (1:1000, Abcam) and a mouse anti-human albumin antibody (1:800, Abcam). Following the addition of HRP-conjugated anti-mouse secondary antibody (1:1000, Vector Laboratories) to each well, color was developed with TMB (3,3',5,5'-tetramethylbenzidine), and reaction was stopped with an equal volume of 2 M $H_2SO_4$. Absorbance at 450 nm was read on an ELISA plate reader (VERSA Max, Molecular Devices).

Figure 6:
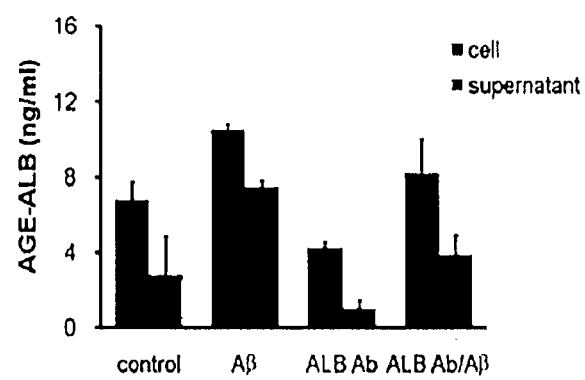
FIG. 6 is a graph showing intracellular and secreted levels of AGE-albumin in human microglial cells as measured by ELISA.

The result is given in FIG. 6.

A significant increase in the level of AGE-albumin was detected in the human microglial cell lysates exposed to Aβ1-42, compared to non-treated lysates. However, the level of AGE-albumin in the cell lysates was decreased upon exposure to an anti-albumin antibody, but increased upon simultaneous exposure to both an anti-albumin antibody and Aβ1-42.

The data obtained above demonstrate that AGE-albumin is synthesized and secreted in human microglial cells.

EXAMPLE 4

Increased Synthesis and Secretion of AGE-Albumin by Oxidative Stress in Human Microglial Cells Aβ1-42 is known to accumulate over a long period of time by oxidative stress. Thus, in order to examine whether the synthesis and secretion of AGE-albumin is directly induced by oxidative stress, human microglial cells were exposed to 0~1000 μM hydrogen peroxide ($H_2O_2$), an inducer of oxidative stress, followed by immunoblot analysis with cell lysates. Also, an immunoblot analysis was performed to examine whether the synthesis and secretion of AGE-albumin in human microglial cells is directly reduced by an antioxidant.

Figure 7:
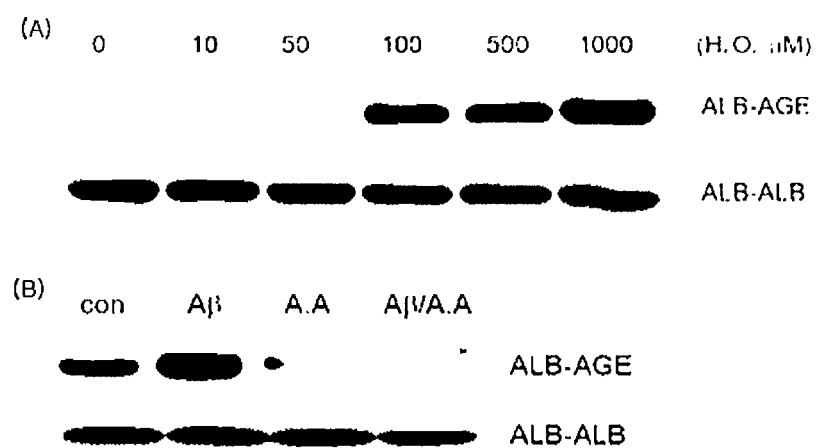
FIG. 7 shows immunoblots of AGE-albumin in human microglial cells illustrating that oxidative stress causes the synthesis and secretion of AGE-albumin in human microglial cells.

The result is given in FIG. 7.

As is apparent from the data of FIG. 7, when the human microglial cells were exposed to hydrogen peroxide ($H_2O_2$), the amount of AGE-albumin was increased in a concentration-dependent manner. By contrast, the addition of the antioxidant ascorbic acid drastically reduced the expression level of AGE-albumin irrespective of Aβ1-42 treatment.

This data suggests that the amounts of both intracellular and secreted AGE-albumin, but not albumin itself, is positively correlated with the degree of oxidative stress. Based on these findings, we conclude that the Aβ-induced synthesis of AGE-albumin in human HMO6 microglial cells and its extracellular secretion is closely related to increased oxidative stress.

The data obtained above indicates that the synthesis and secretion of AGE-albumin in human microglial cells is positively correlated with oxidative stress because oxidative stress accumulates Aβ1-42 in human microglial cells, which induces the synthesis of AGE-albumin.

EXAMPLE 5

Aβ1-42 Polymerization by AGE-Albumin Synthesized and Secreted in Human Microglial Cells of Alzheimer's Disease Model (ThT Fluorescence Assay)

Albumin is known as a potent inhibitor of amyloidbeta 1-42 (Aβ1-42), and approximately 60% of the amyloid inhibitory activity isolated from cerebrospinal fluid (CSF) is accounted for by albumin, suggesting that albumin may directly interact with Aβ. Thus far, however, it has largely not been known whether the amount and distribution of AGE-albumin correlate positively with amyloid plaques. Hence, interaction between AGE-albumin synthesized and secreted in microglial cells of an Alzheimer's disease model and Aβ1-42 aggregation were examined using a ThT (thioflavin T) fluorescence assay.

Aβ1-42-treated rat brain tissues and human brain tissues from Alzheimer's disease patients were separately incubated at 37° C. for 2.5 hrs with 10 mM albumin or AGE-albumin with constant shaking. ThT emission fluorescence was measured at 483 nm (450 nm excitation) with a Perkin-Elmer luminescence spectrophotometer (LS-55). Fluorescence values for albumin- or AGE-albumin-exposed cells were normalized to the DMSO-treated negative control and expressed as percentage relative fluorescence.

Figure 8:
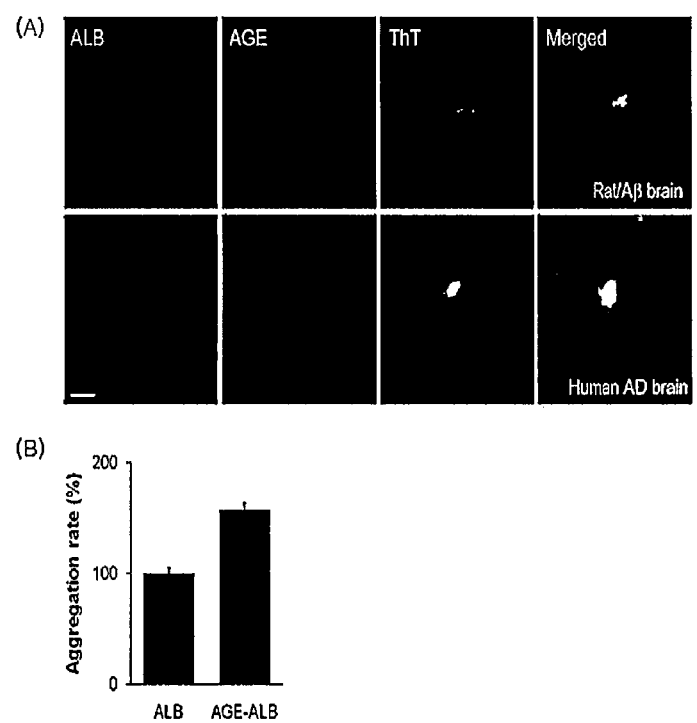
FIG. 8 shows the induction of Aβ1-42 aggregation by the AGE-albumin synthesized and secreted in the Aβ1-42-treated rat brain tissues and the human brain tissues of Alzheimer's patients, as demonstrated by ThT fluorescence assay.

The results are shown in FIG. 8.

As is apparent from FIG. 8, AGE-albumin and amyloid plaques were co-localized in the Aβ1-42-treated rat brain tissues and the human brain tissues of Alzheimer's patients (A), and the aggregation of Aβ1-42 was significantly increased after exposure of microglial cells to AGE-albumin, compared to albumin alone (B). Therefore, these results suggest that AGE-albumin induces Aβ1-42 aggregation in Aβ1-42-treated rat brain tissues and human brain tissues of Alzheimer's disease patients.

EXAMPLE 6

Aβ1-42 Synthesis by AGE-Albumin in Human Microglial Cells

To determine whether AGE-albumin induces Aβ1-42 synthesis in human microglial cells, the cells, after exposure to AGE-albumin, were analyzed for Aβ1-42 level by ELISA, and for the localization and level of BACE, ADAM10, and APP, by immunohistochemistry and immunoblot analysis, respectively.

Figure 9:
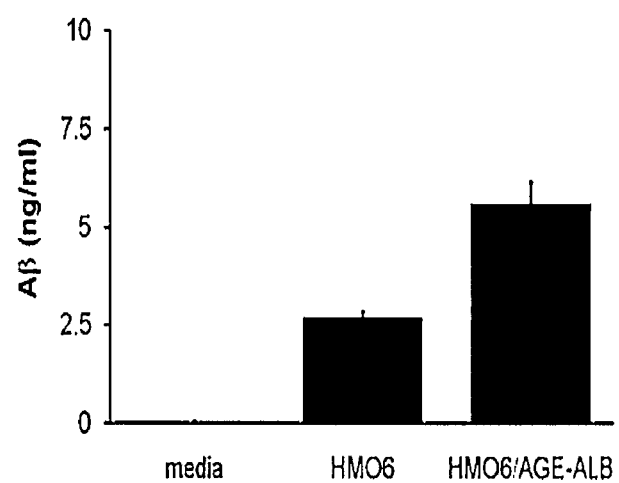
FIG. 9 is a graph in which expression levels of Aβ1-42 in human microglial cells exposed to AGE-albumin are represented, as measured by ELISA.
Figure 10:
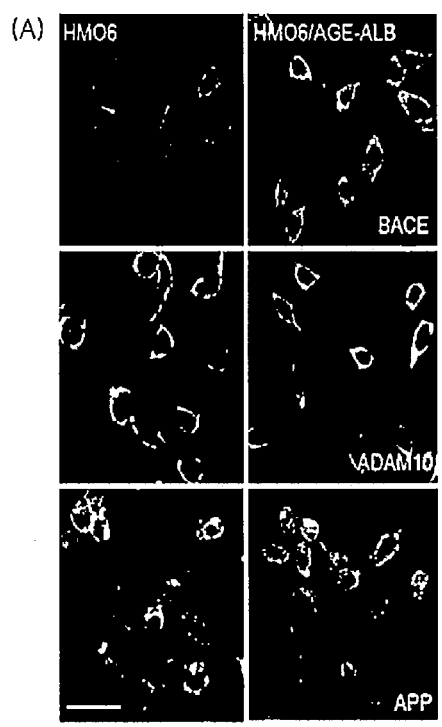
FIG. 10 shows the localization and the level of BACE, ADAM10, and APP in human microglial cells exposed to AGE-albumin as determined by immunohistochemical staining (A) and immunoblotting (B), respectively.
Figure 10:
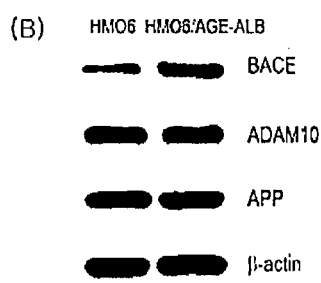

ELISA results for Aβ1-42 levels in human microglial cells exposed to AGE-albumin are shown in FIG. 9. FIG. 10 shows the localization and the level of BACE, ADAM10, and APP in human microglial cells exposed to AGE-albumin as determined by immunohistochemical staining (A) and immunoblotting (B), respectively.

As shown in FIG. 9, AGE-albumin increased the level of Aβ1-42 in human microglial cells.

In human microglial cells, as is understood from FIG. 10, AGE-albumin upregulated BACE, but had no influence on the levels of ADAM10 and APP.

These results suggest that AGE-albumin induces the synthesis of Aβ1-42 in human microglial cells.

EXAMPLE 7

Induction of Cell Death by AGE-Albumin in Primary Human Neuronal Cells

Stress-activated Mitogen-Activated Protein Kinase (MAPK) is reported to play a critical role in apoptosis. Hence, experiments were carried out to examine whether AGE-albumin directly activates the MAPK signaling pathway and increases the expression level of Bax in primary human neuronal cells, as follows.

1. Culture of Primary Human Neuronal Cells

Primary human neuronal cells were prepared from human brain tissues. The brain tissue collection and usage were approved by the Ethics Committee of the Seoul National University College of Medicine, Seoul, Korea. Small pieces of human brain cortexes were incubated with phosphate-buffered saline (PBS) containing 0.25% trypsin and 40 mg/ml DNase I for 30 min at 37° C. Dissociated cells were suspended in DMEM containing 5% FBS, 5% HS (horse serum), 20 mg/mL gentamicin and 2.5 mg/mL amphotericin B, plated at a density of $1 \times 10^6$ cells/mL (10 mL) into 10 cm culture dishes, and maintained at 37° C. in a 5% $CO_2$/95% atmosphere in an incubator. After 2-3 weeks of in vitro culture, buoyant cells in the culture dishes were harvested and plated again onto a Lab-Tek II Chamber Slide System ($2 \times 10^4$ cells/well, Nunc) for immunofluorescence to prepare microglial cell-enriched cells. The other cells were treated with AGE-albumin and used in analyzing apoptosis-related properties.

2. Immunohistochemistry and Immunoblotting

Cell lysates from primary human neuronal cells before and after AGE-albumin treatment were analyzed for the localization and level of RAGE, ERK1/2, pERK1/2, p38, pp38, SAPK/JNK, pSAPK/JNK, and Bax by immunohistochemistry and immunoblotting.

Figure 11:
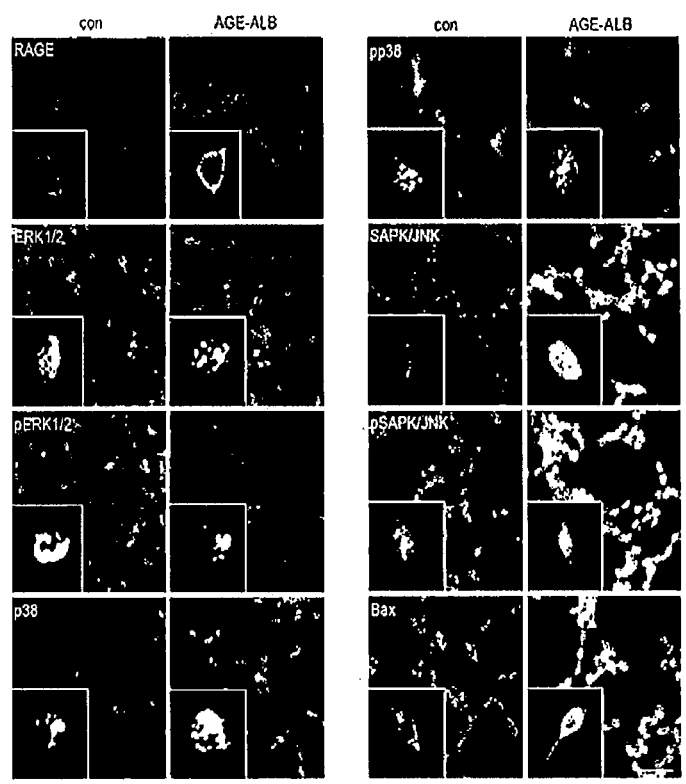
FIG. 11 shows the localization and the level of RAGE, ERK1/2, pERK1/2, p38, pp38, SAPK/JNK, pSAPK/JNK, and Bax in primary human neuronal cells exposed to AGE-albumin as determined by immunohistochemical staining.
Figure 12:
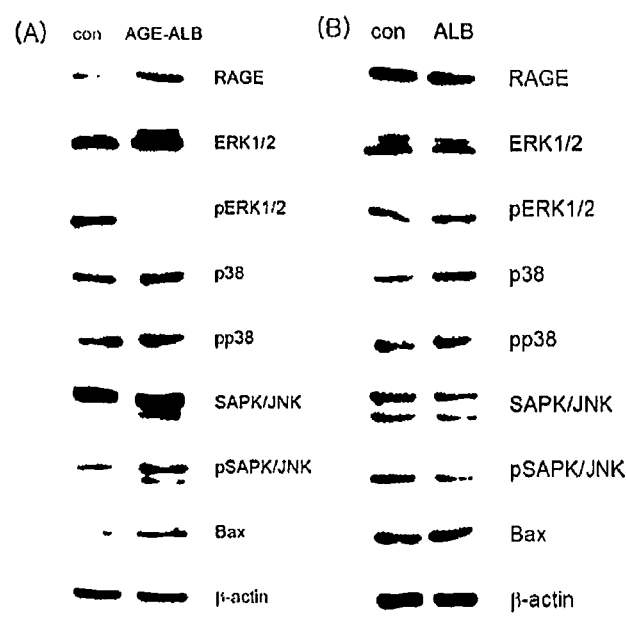
FIG. 12 shows the localization and the level of RAGE, ERK1/2, pERK1/2, p38, pp38, SAPK/JNK, pSAPK/JNK, and Bax in primary human neuronal cells exposed to AGE-albumin as determined by immunoblotting.

FIGS. 11 and 12 show the localization and the level of RAGE, ERK1/2, pERK1/2, p38, pp38, SAPK/JNK, pSAPK/JNK, and Bax in primary human neuronal cells exposed to AGE-albumin as determined by immunohistochemical staining and immunoblotting, respectively.

As can be seen in FIGS. 11 and 12, the level of RAGE was significantly increased after the primary human neuronal cells were exposed to AGE-albumin. Also, significant increases were observed in the levels of ERK1/2, p38, pp38, SAPK/JNK, and pSAPK/JNK, but not pERK1/2, by AGE-albumin, thus activating MAPK and Bax, a pro-apoptotic protein.

3. Interaction Between AGE and RAGE in Primary Human Neuronal Cells Proximity Ligation Assay (PLA)

An examination was made of the interaction between AGE and RAGE in cell lysates from primary human neuronal cells before and after AGE-albumin treatment. For this, PLA was performed with primary human neuronal cells and brain tissues to visualize the interaction between AGE and RAGE.

Target tissues were rinsed with chilled PBS, and incubated overnight at 4° C. with a mouse anti-human albumin antibody (1:200, R&D system), a rabbit anti-AR antibody (1:100, Chemicon), or an anti-RAGE antibody (1:200, Santa Cruz). PLA and Hoechst staining were carried out using a Duolink Detection Kit (O-link Bioscience) according to the manufacturer's protocol. Tissue specimens were mounted onto slides using Vectashield mounting media (Vector Laboratories) and analyzed under a confocal microscope (LSM 710). The number of in situ PLA signals per cell was counted using the semi-automated image analysis program Blob-FinderV3.0.

Figure 13:
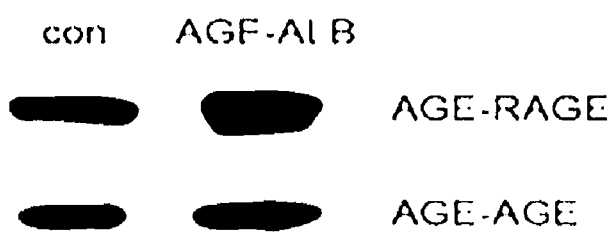
FIG. 13 shows AGE-RAGE interaction in cell lysates from primary human neuronal cells before and after exposure to AGE-albumin.

FIG. 13 shows AGE-RAGE interaction in cell lysates from primary human neuronal cells before and after exposure to AGE-albumin.

As seen in FIG. 13, the amount of AGE-RAGE interaction was significantly increased in primary human neuronal cells exposed to AGE-albumin.

4. Change of Intracellular Calcium Level

Primary human neuronal cells were grown on Lab-Tek II glass slide chambers (Nunc). After 2 days of cell culture, cells were incubated with 4 µM Fluo-3 dye (Life Technology) for 40 min at 37° C. Thereafter, the cells were subjected to image analysis with a laser confocal fluorescence microscope (LSM 710, Carl Zeiss). Upon adjusting proper fields, 100 ng/ml of AGE-albumin was carefully added into the slide chamber to record any changes in intracellular calcium levels during the first 20 min.

Figure 14:
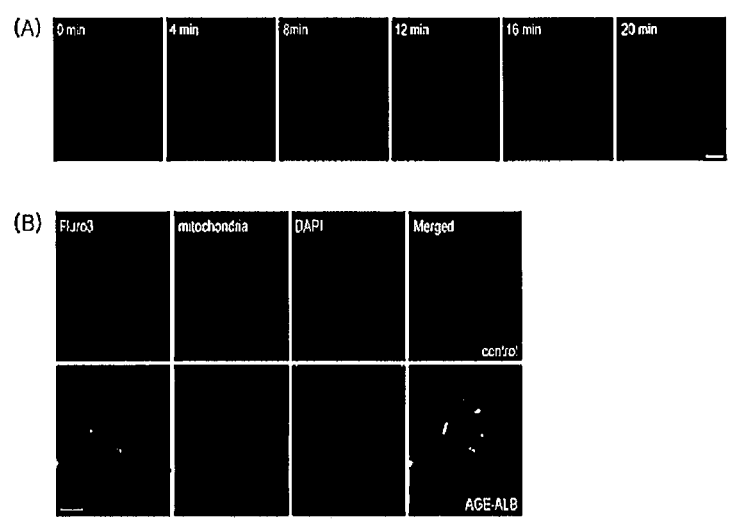
FIG. 14 shows laser confocal fluorescence microphotographs of primary human neuronal cells exposed to AGE-albumin, illustrating changes in mitochondrial calcium influx.

The result is given in FIG. 14.

As can be seen in FIG. 14, primary human neuronal cells exposed to AGE-albumin were allowed to increase mitochondrial calcium influx.

5. Cell Viability (MTT Assay)

To confirm that AGE-albumin induces the expression of Bax in primary human neuronal cells, which increases mitochondrial calcium influx, finally leading to the induction of cell death, the following experiment was carried out.

Primary human neuronal cells were seeded at a density of $2 \times 10^3$ cells/well into 96-well plates. When reaching 80% confluence, the primary human neuronal cells were treated with various concentrations (0, 0.01, 0.1, 1, 10, 20 µg/mL) of AGE-albumin, or various concentrations (0, 0.5, 1, 5, 10 mg/mL) of albumin. After 24 hours of treatment, the cells were rinsed with PBS and examined for viability using an MTT [3-(4,5-dimethylthiazol-2-yl)-2,5-diphenyl tetrazolium bromide] assay. Absorbance in each well was read at 540 nm on a 96-well plate reader (VERSA Max, Molecular Devices).

Figure 15:
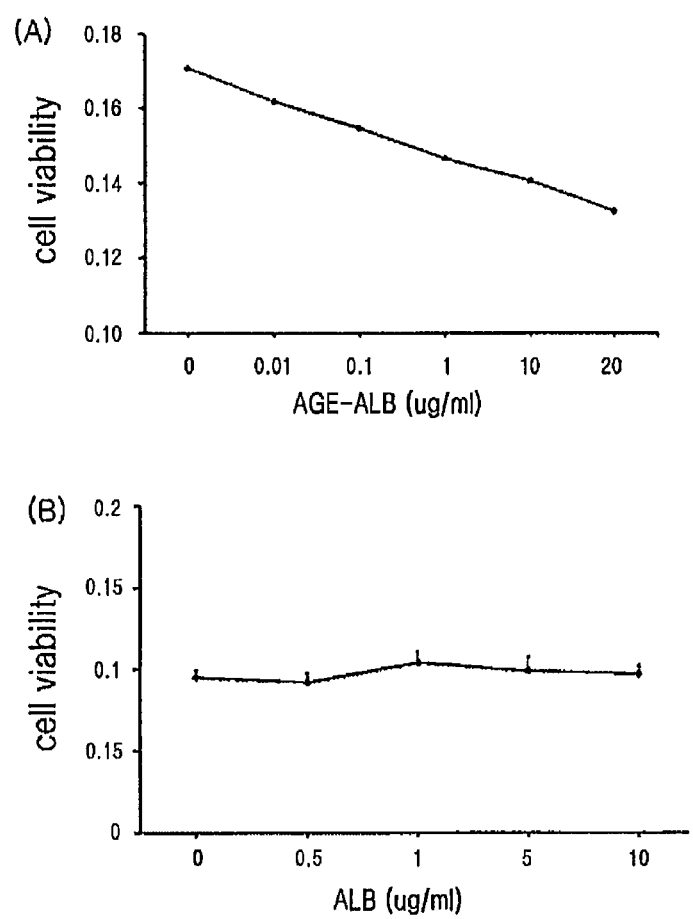
FIG. 15 shows graphs in which the cell viability of primary human neuronal cells is plotted against AGE-albumin, as measured by MTT assay.

The results are given in FIG. 15.

When primary human neuronal cells were treated with AGE-albumin, as seen in FIG. 15, the cell viability decreases with an increase in AGE-albumin concentration, indicating that AGE-albumin induces cell death. In contrast, when primary human neuronal cells were treated with albumin alone, the cell viability remained almost unchanged irrespective of albumin concentration, indicating that albumin does not induce cell death.

These results are evidence demonstrating that AGE-albumin stimulates primary human neuronal cells to upregulate RAGE, which triggers a subsequent complex pathologic cascade including the MAPK signaling transduction pathway, Bax activation, and mitochondrial calcium influx, leading to cell death.

EXAMPLE 8

Distribution and Localization of AGE-Albumin in Mouse Blood Monocytes

To examine the distribution and localization of AGE-albumin in mouse blood monocytes, the cells before and after Aβ1-42 treatment were immunostained with triple labels for albumin (green), AGE (red), and DAPI (blue) and observed under a laser confocal fluorescence microscope.

Figure 16:
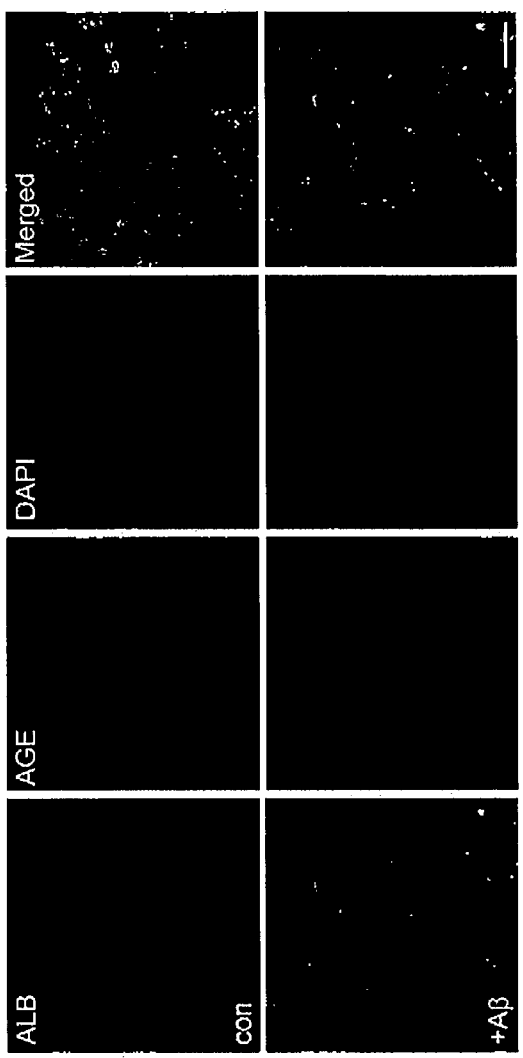
FIG. 16 shows laser confocal fluorescence microphotographs of mouse blood monocytes before and after Aβ1-42 treatment, representing the distribution and localization of AGE-albumin by use of antibodies.

The results are given in FIG. 16.

As can be seen in FIG. 16, albumin (green) was co-localized with AGE (red) in mouse blood monocytes before and after Aβ1-42 treatment. In addition, the mouse blood monocytes treated with Aβ1-42 were observed to have a wider distribution of albumin and AGE and a higher expression level of AGE-albumin, compared to non-treated cells.

EXAMPLE 9

Protection by Soluble RAGE (sRAGE) Against Aβ1-42-Mediated Neuronal Death: In Vivo Assay To investigate the protective effect of sRAGE against Aβ-mediated neuronal death, an in vivo assay was performed after injection of Aβ alone or co-injection of Aβ and sRAGE (Aβ/sRAGE) into rat brain.

1. Animal Model

Sprague-Dawley rats, each weighing 230-350 g, were used as experimental animals. The rats were maintained on a 12-h light-dark cycle, allowed to have access to food and water ad libitum, and acclimated for at least 1 week prior to usage. All animal experiments were approved by the Institute Animal Care and Use Committee, and were conducted humanely.

Animals were anaesthetized with ketamine (0.75 mg/kg body weight) and rompun (0.2 mg/kg body weight) prior to surgical procedures. For in vivo treatments, PBS and sRAGE were dissolved at a concentration of 400 µM in sterile water and kept at 4° C. until use. The head was fixed on a stereotaxic instrument before a midline incision of the scalp skin was made. The skull was pierced with a biological electric drill at the bregma (posteriorly, 8.3 mm; laterally, 5.4 mm) and the needle (gauge 30) on a 5-µL Hamilton syringe was lowered vertically until it reached the target area (depth, 4.5 mm). Five microliters of 200 µM Aβ1-42, 200 µM Aβ1-42/sRAGE, or phosphate buffered saline (PBS) were injected slowly at the rate of 1 µL per minute with an automatic microinjector. Thereafter, the syringe was removed slowly and surgical wounds were sutured with wound clips followed by topical treatment with antibiotics.

Most rats were recovered after a total of 3 days post injection. After full recovery, all rats were re-anaesthetized in the same manner, and perfused transcardially with 100~200 mL of heparinized saline at 18° C. followed by 400 mL of 4% paraformaldehyde-lysine periodate in a 0.1 M sodium phosphate buffer (pH, 7.4). The brains were removed, placed in the same fixative for 4 hrs at 4° C., and then transferred into ice-cold 0.1 M phosphate-buffered saline (PBS) containing 20% sucrose. The brains were cut in a transverse plane at a 10 µm thickness with a freezing microtome and were stored at −80° C. until use.

2. Number of Neuronal Cells in Rat Brain Tissues

The relative levels of neurons in rat brain tissues were evaluated by cresyl violet staining after Aβ injection without or with sRAGE co-treatment (Aβ/sRAGE) for 72 hrs before microscopy.

Figure 17:
FIG. 17 shows microphotographs taken from rat brain tissues stained with cresyl violet 72 hours after exposure to Aβ1-42 alone or in combination with sRAGE(Aβ/sRAGE) in which the relative levels of neurons are determined.

The results are given in FIG. 17.

As seen in FIG. 17, the relative levels of neurons in rat brains were dramatically increased after Aβ1-42 and sRAGE (Aβ/sRAGE) were co-injected compared to those administered with Aβ1-42 alone.

3. Distribution and Localization of AGE-Albumin in Rat Brain Tissue

To examine the distribution and localization of AGE-albumin in rat brain tissues treated with Aβ1-42 alone or in combination with sRAGE (Aβ/sRAGE), immunohistochemistry (IHC) was performed to immunostain the brain tissues with triple labels for AGE (red), albumin (green), and microglial cells (Iba1, blue), followed by laser confocal fluorescence microscopy to determine the level of AGE-albumin.

Figure 18:
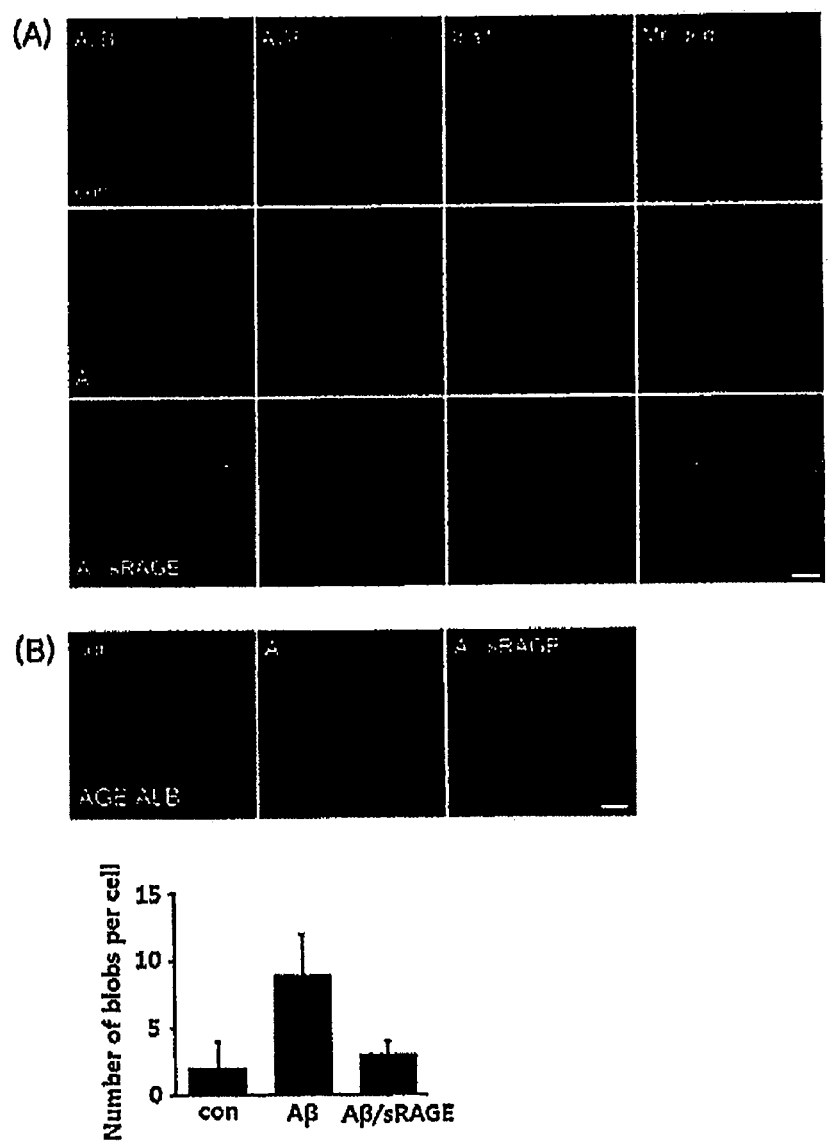
FIG. 18 shows the distribution and localization of AGE-albumin in rat brain tissues treated with Aβ1-42 alone or in combination with sRAGE (Aβ/sRAGE) after immunostaining the brain tissues with triple labels for AGE (red), albumin (green), and microglial cells (Iba1, blue), as measured by laser confocal fluorescence microscopy (A), and the relative densities of AGE-albumin in a graph (B).

The results are given in FIG. 18.

As can be seen in FIG. 18, the relative numbers of AGE, albumin, and Iba1 (microglial cells) positive cells were increased in Aβ1-42-injected rat brains, but decreased in Aβ/sRAGE-exposed rat brains. In addition, a remarkably higher level of AGE-albumin was detected in rat brain tissues injected with Aβ1-42 than with Aβ1-42 and sRAGE (Aβ/sRAGE).

4. Distribution and Localization of RAGE, NeuN, DAPI, Bax and p-SAPK/JNK in Rat Brain Tissue To examine whether Aβ1-42 induces neuronal cell death and sRAGE protects neuronal cells from RAGE-mediated cell death in rat brain tissues, immunohistochemistry (IHC) was performed on rat brain tissues exposed to Aβ1-42 alone or in combination with sRAGE (Aβ/sRAGE) to immunostain the tissues with labels for RAGE, NeuN, DAPI, Bax, and p-SAPK/JNK. Then, their distribution and localization were observed under a laser confocal fluorescence microscope.

Figure 19:
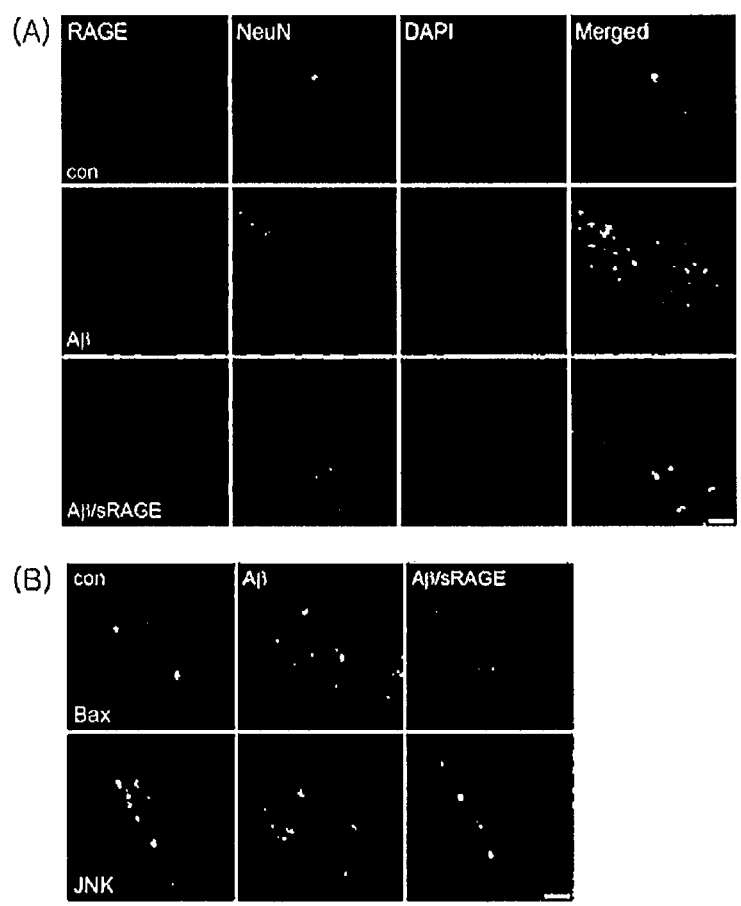
FIG. 19 shows laser confocal fluorescence microphotographs taken from rat brain tissues exposed to Aβ1-42 alone or in combination with sRAGE (Aβ/sRAGE) in which the distributions and localizations of RAGE, NeuN, DAPI, Bax, and p-SAPK/JNK are represented, as analyzed by immunoblotting with respective antibodies.

The results are given in FIG. 19.

Expression levels of RAGE, NeuN, DAPI, Bax, and p-SAPK/JNK in rat brain tissues, as shown in FIG. 19, were increased after injection with Aβ1-42 alone, but decreased after injection with Aβ1-42 and sRAGE (Aβ/sRAGE), indicating that Aβ1-42 induces neuronal cell death whereas sRAGE protects neurons from RAGE-mediated cell death.

EXAMPLE 10

Distribution and Localization of AGE-Albumin in Brain Tissues of Stroke Patients The distribution and localization of AGE-albumin in brain tissues of stroke patients was examined using laser confocal microscopy following carrying out immunohistochemistry (IHC) to immunostain the brain tissues with labels for AGE and albumin.

Figure 20:
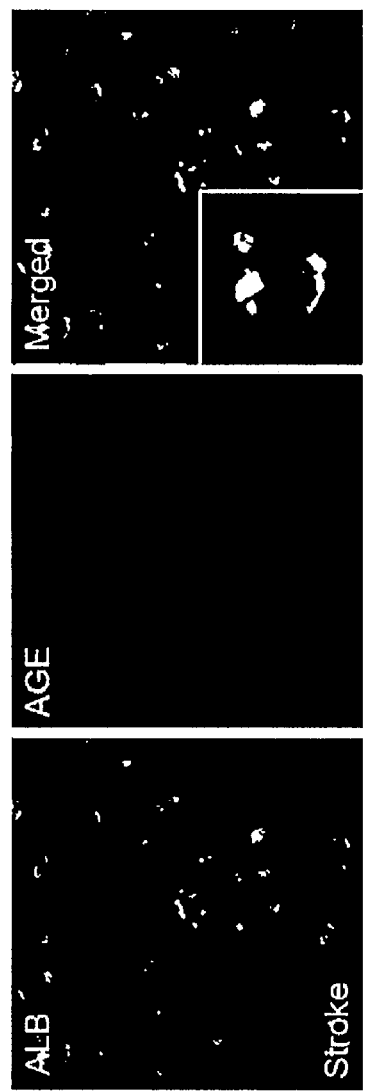
FIG. 20 shows laser confocal fluorescence microphotographs taken from brain tissues of stroke patients in which the distribution and localization of AGE-albumin was represented as analyzed by immunohistochemistry with antibodies.

The results are given in FIG. 20.

Albumin (green) was, as shown in FIG. 20, co-localized with AGE (red), with a wide distribution of AGE-albumin in the brain tissues of stroke patients.

EXAMPLE 11

Expression of Hypoxia Inducible Factor (HIF-1α) and HMGB1 (High Motility Group Protein B1) in Human Microglial Cell Models of Stroke To examine expression levels of HIF-1α and HMGB1 in human microglial cell models of stroke, the following experiments were carried out.

1. Cell Culture and Construction of Cell Model of Stroke

Human microglial cells were cultured at 37° C. in DMEM (Gibco, 10% FBS (Gibco), 0.1% gentamicin (Gibco), a high concentration of glucose) at 37° C. in a 5% $CO_2$ incubator. Then, the microglial cells were exposed to glucose-free DMEM for 1 hr within a hypoxic (5% $CO_2$ and 95% $N_2$) chamber (Billups-Rothenberg, Del Mar, Calif.) to prepare a cell model of stroke.

2. Expression of HIF-1α and HMGB1 in Human Microglial Cell Models of Stroke

An examination was made of the expression of HIF-1α and HMGB1 in human microglial cells of an oxygen- and glucose-deprived model of stroke by immunohistochemistry (IHC), PCR and immunoblotting.

Figure 21:
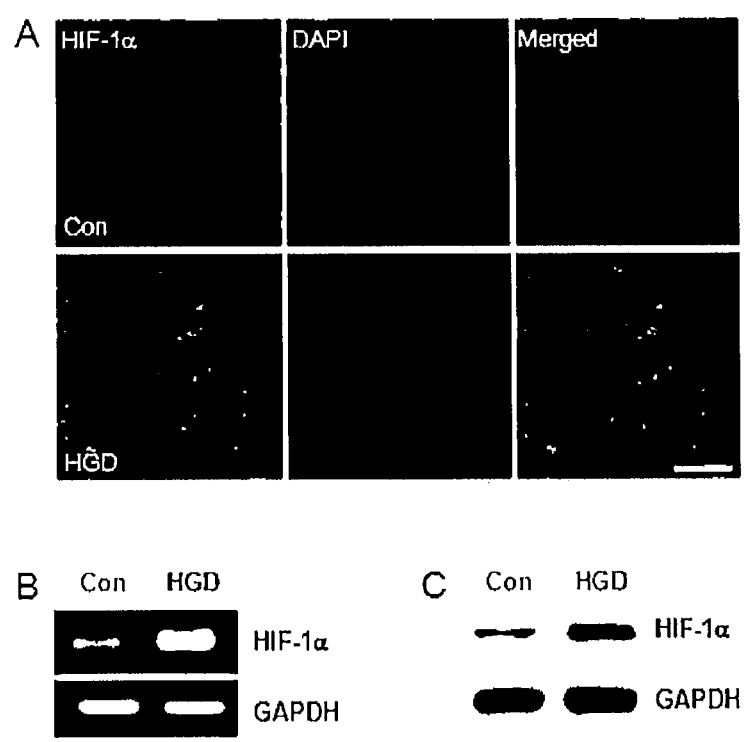
FIG. 21 shows the expression level of hypoxia inducible factor (HIF-1α) in human microglial cells of an oxygen and glucose deprivation model of stroke, as analyzed by immunohistochemistry (IHC) (A), PCR (B), and immunoblotting (C).
Figure 22:
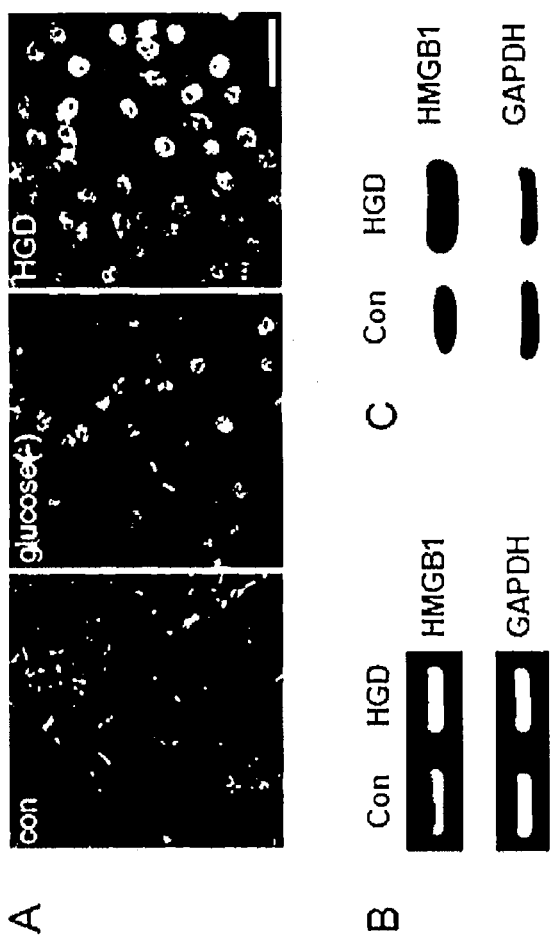
FIG. 22 shows the expression level of HMGB1 (high motility group protein B1) in human microglial cells in an oxygen and glucose deprivation model of stroke, as analyzed by immunohistochemistry (IHC) (A), PCR (B), and immunoblotting (C).

Expression levels of HIF-1α and HMGB1 in human microglial cells of an oxygen and glucose deprivation model of stroke are given in FIGS. 21 and 22, respectively.

As can be seen in FIGS. 21 and 22, human microglial cells of a hypoxic and glucose-deprived model of stroke had increased levels of HIF-1α and HMGB1.

EXAMPLE 12

Synthesis and Secretion of AGE-Albumin in Human Microglial Cell Model of Stroke

1. Expression Level of AGE-Albumin in Human Microglial Cell Model of Stroke

An examination was made of the synthesis and secretion of AGE-albumin in human microglial cells of an oxygen- and glucose-deprived model of stroke. For this, its expression level was measured using immunohistochemistry (IHC), immunoblotting, and ELISA.

Figure 23:
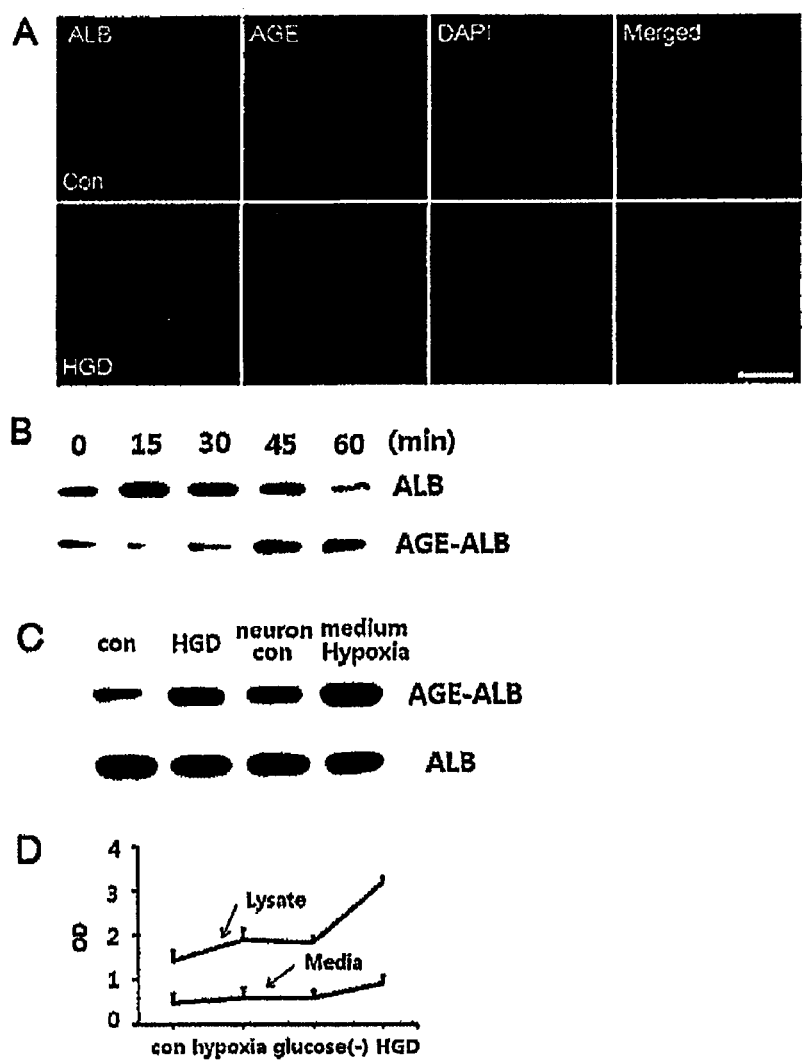
FIG. 23 shows the expression level of AGE-albumin in human microglial cells of an oxygen and glucose deprivation model of stroke, as analyzed by immunohistochemistry (IHC) (A), immunoblotting (B, C), and ELISA (D).

The results are given in FIG. 23.

The expression level of AGE-albumin was significantly increased in human microglial cells of an oxygen- and glucose-deprived model of stroke, as shown in FIG. 23.

2. Change of Intracellular and Secreted Levels of AGE-Albumin in Human Microglial Cell Model of Stroke with Concentration of HMGB1

Human microglial cell models of stroke were treated with HMGB1, which is known to secrete most abundantly upon stroke to excite microglial cells. Expression levels of AGE-albumin in the human microglial cell model of stroke were quantitated at various concentrations (0, 50, 200, 500, 2000 ng/mL) of HMGB1 using immunohistochemistry (IHC), ELISA, and immunoblotting.

Figure 24:
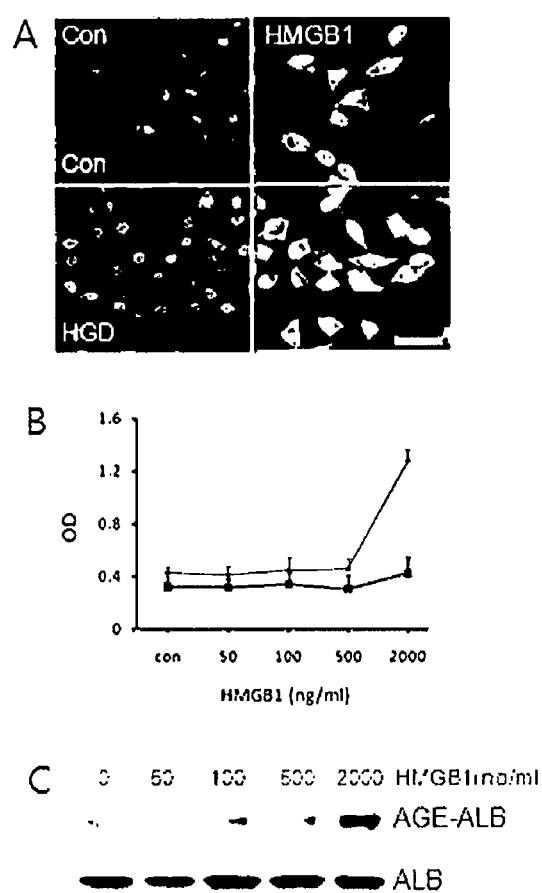
FIG. 24 shows expression levels of AGE-albumin in the human microglial cell model of stroke, as quantitated at various concentrations (0, 50, 200, 500, 2000 ng/mL) of HMGB1 using immunohistochemistry (IHC) (A), ELISA (B), and immunoblotting (C).

The results are shown in FIG. 24.

As can be seen in FIG. 24, the expression level of AGE-albumin in human microglial cells of a hypoxic and glycose-deprived model of stroke significantly increased with an increase in the concentration of HMGB1.

3. Change of Intracellular and Secreted Level of AGE-Albumin in Human Microglial Cell Model of Stroke with Concentration of HMGB1 Inhibitor A Human microglial cell model of stroke was exposed to various concentrations (0, 50, 200, 500, 2000 ng/mL) of the HMGB1 inhibitor glycyrrhizic acid, and quantitatively analyzed for AGE-albumin using ELISA and immunoblotting.

Figure 25:
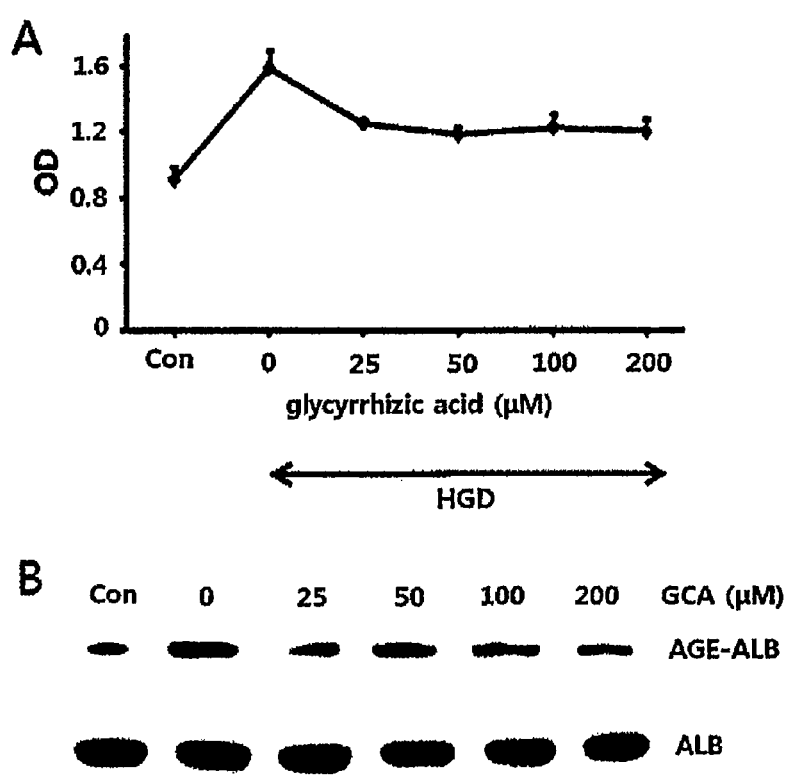
FIG. 25 shows expression levels of AGE-albumin in the human microglial cell model of stroke, as quantitated at various concentrations (0, 50, 200, 500, 2000 ng/mL) of the HMGB1 inhibitor glycyrrhizic acid using ELISA, and immunoblotting.

The results are given in FIG. 25.

The expression level of AGE-albumin in the human microglial cells of a hypoxic and glucose-deprived model of stroke, as can be seen in FIG. 25, significantly decreased with an increase in the concentration of the HMGB1 inhibitor.

EXAMPLE 13

Increased Synthesis and Secretion of AGE-Albumin by Oxidative Stress in Human Microglial Cell Model of Stroke In order to examine whether the synthesis and secretion of AGE-albumin in the human microglial cell model of stroke is directly induced by oxidative stress, the human microglial cells were exposed to 0~1000 µM hydrogen peroxide ($H_2O_2$), an inducer of oxidative stress, followed by immunoblot analysis with cell lysates. Also, an immunoblot analysis was performed to examine whether the synthesis and secretion of AGE-albumin in the human microglial cell model of stroke is directly reduced by ascorbic acid, an antioxidant.

Figure 26:
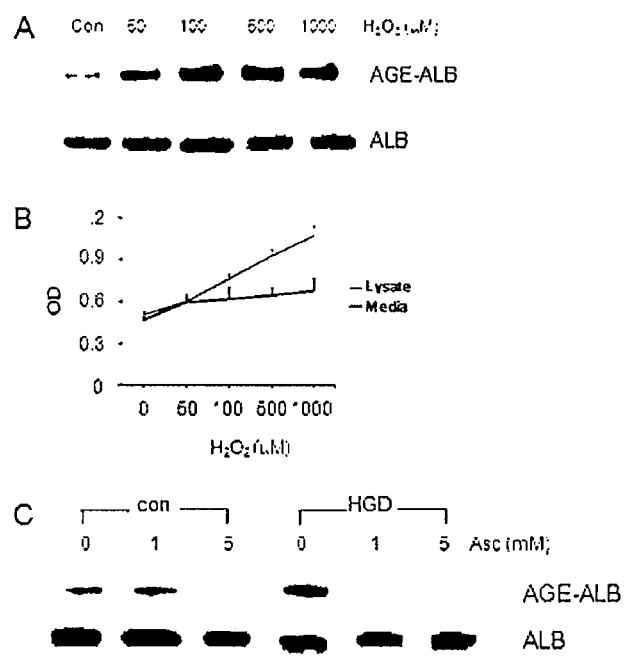
FIG. 26 shows that the synthesis and secretion of AGE-albumin in the human microglial cell model of stroke is directly induced by oxidative stress, as analyzed by immunoblotting.

The result is given in FIG. 26.

As is apparent from the data of FIG. 26, when the human microglial cells of a model of stroke were exposed to hydrogen peroxide ($H_2O_2$), the amount of AGE-albumin was increased in a concentration-dependent manner. In contrast, the addition of the antioxidant ascorbic acid drastically reduced the expression level of AGE-albumin irrespective of hypoxia and glucose deprivation.

EXAMPLE 14

Induction of Neuronal Cell Death by AGE-Albumin in Primary Human Neuronal Cells

Experiments were carried out to examine whether AGE-albumin induces neuronal death in primary human neuronal cells, as follows.

1. Culture of Primary Human Neuronal Cells

Primary human neuronal cells were grown in DMEM (Gibco, 10% FBS (Gibco), 0.1% gentamicin (Gibco), a high concentration of glucose) at 37° C. in a 5% $CO_2$ incubator. The cultured cells were incubated for 24 hrs with AGE-albumin (Sigma, 10 µg/mL) before use in the following experiments.

2. Immunohistochemistry and Immunoblotting

To examine whether AGE-albumin directly activates the MAPK signaling pathway and upregulates Bax in the primary human neuronal cells from human brain tissues, cell lysates from primary human neuronal cells before and after AGE-albumin treatment were analyzed for the expression level of RAGE, ERK1/2, pERK1/2, p38, pp38, SAPK/JNK, pSAPK/JNK, and Bax by immunohistochemistry and immunoblotting.

Figure 27:
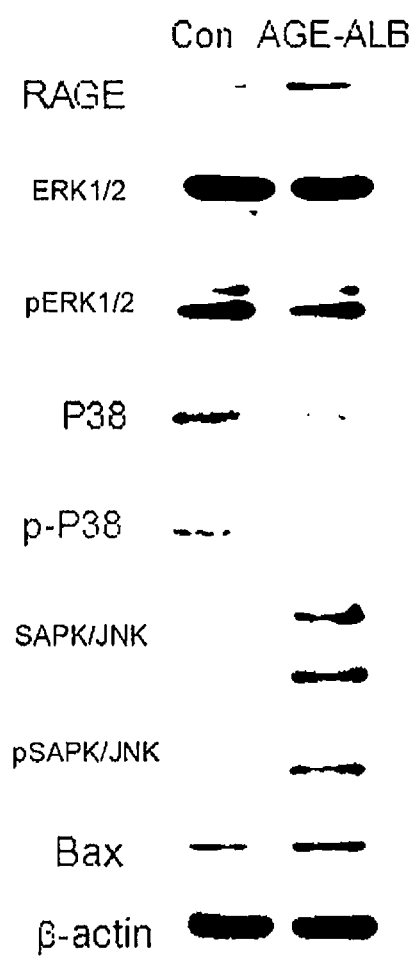
FIG. 27 shows immunoblots representing expression levels of RAGE, ERK1/2, p-ERK1/2, p38, p-p38, SAPK/JNK, p-SAPK/JNK, and Bax in primary human neuronal cells of human brain tissues exposed to AGE-albumin.

The results are given in FIG. 27.

As can be seen in FIG. 27, the level of RAGE was significantly increased after the primary human neuronal cells were exposed to AGE-albumin. Also, significant increases were observed in the levels of SAPK/JNK and pSAPK/JNK, but not pERK1/2, p38, and pp38, by AGE-albumin, thus activating MAPK and Bax, a pro-apoptotic protein.

3. Cell Viability (MTT Assay) and Protection of Neuronal Cells from Cell Death by sRAGE An examination was made to see if an elevated level of Bax in AGE-albumin-exposed primary human neuronal cells leads to neuronal death. In this regard, primary human neuronal cells were seeded at a density of $2 \times 10^3$ cells/well into 96-well plates. When reaching 80% confluence, the primary human neuronal cells were treated with various concentrations (0, 0.1, 1, 10, 50 µg/mL) of AGE-albumin. After 24 hours of treatment, the cells were rinsed with PBS and examined for viability using an MTT [3-(4,5-dimethylthiazol-2-yl)-2,5-diphenyl tetrazolium bromide] assay. Absorbance in each well was read at 540 nm.

To examine the protective effect of soluble RAGE (sRAGE) on neuronal cells against cell death, human microglial cells were treated with sRAGE alone, AGE-albumin alone, or sRAGE/AGE-albumin, followed by measuring absorbance at 540 nm.

Figure 28:
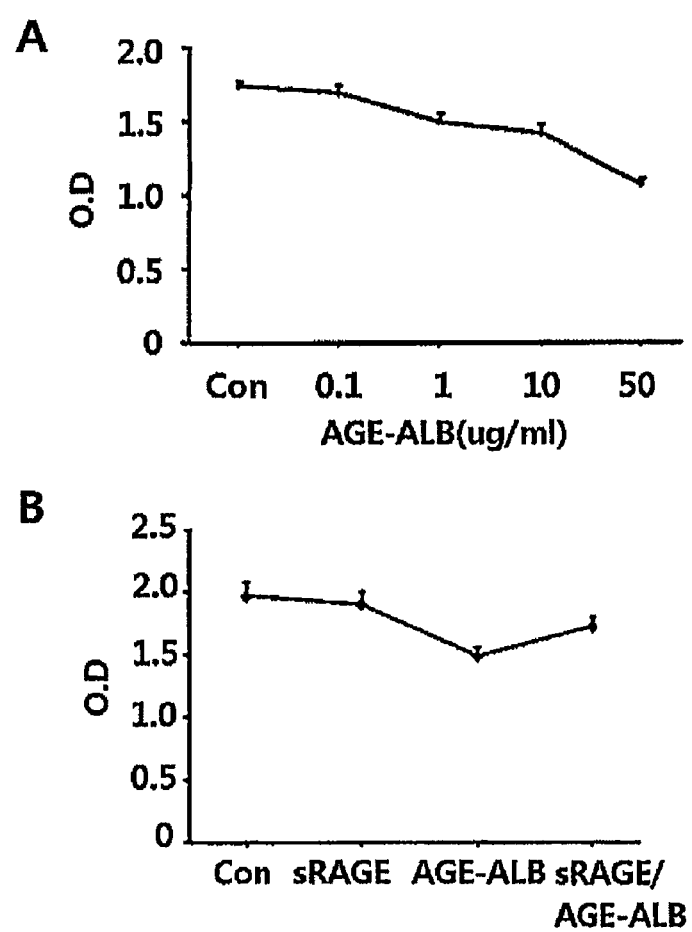
FIG. 28 shows the cell viability of primary neuronal cells exposed to AGE-albumin, as measured by MTT assay (A), and the protective effect of sRAGE on neuronal cells against cell death (B).

The results are given in FIG. 28.

As is understood from the data of FIG. 28, cell viability was reduced with an increase in the concentration of AGE-albumin (A), but increased upon simultaneous exposure to sRAGE and AGE-albumin (B). Therefore, this data demonstrate that AGE-albumin induces neuronal cell death while sRAGE protects neuronal cells from AGE-albumin-induced neuronal cell death.

EXAMPLE 15

Distribution and Localization of AGE-Albumin in Brain Tissues of Parkinson's Disease Patients The distribution and localization of AGE-albumin in brain tissues of Parkinson's disease patients was examined using laser confocal microscopy following carrying out immunohistochemistry (IHC) to immunostain the brain tissues with labels for AGE, albumin, microglial cell (Iba1), and AGE-albumin.

Figure 29:
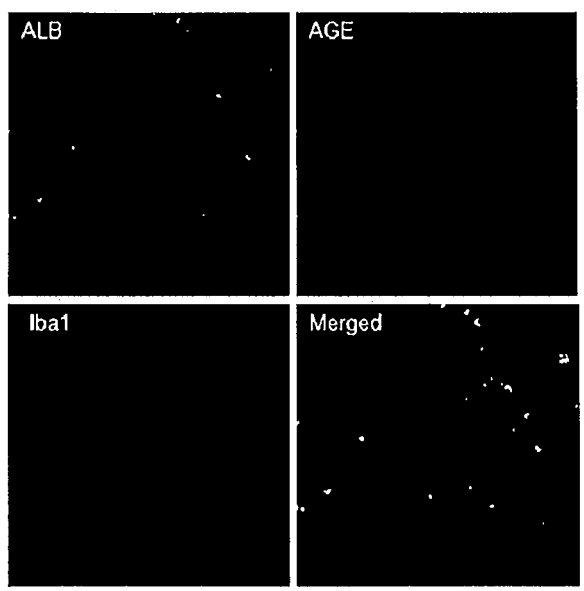
FIG. 29 shows laser confocal fluorescence microphotographs taken from brain tissues of Parkinson's disease patient in which the distribution and localization of AGE-albumin is represented by immunostaining with antibodies.

The results are given in FIG. 29.

Albumin (green) was, as shown in FIG. 29, co-localized with AGE (red), with a wide distribution of AGE-albumin in the brain tissues of Parkinson's disease patients. Also, Iba1 was detected at the same positions as AGE-albumin over a wide region.

EXAMPLE 16

Expression of α-Synuclein or TNF-α in Human Microglial Cell Model of Parkinson's Disease To examine expression levels of α-synuclein and TNF-α in human microglial cell models of Parkinson's disease, the following experiments were carried out.

1. Cell culture and Construction of Cell Model of Parkinson's Disease

Human microglial cells were cultured at 37° C. in DMEM (Gibco, 10% FBS (Gibco), 0.1% gentamicin (Gibco), a high concentration of glucose) at 37° C. in a 5% $CO_2$ incubator. Then, the microglial cells were exposed to rotenone (Sigma, 1 nM), a causative agent of Parkinson's disease, for 10 days or to 6-hydroxydopamine (6-OHDA) for 24 hrs to prepare a cell model of Parkinson's disease.

2. Expression of α-Synuclein or TNF-α in Human Microglial Cell Models of Parkinson's Disease α-Synuclein or TNF-α is present at a high level in the brain tissue of Parkinson's disease patients. Hence, human microglial cells after treatment with the Parkinson's disease causing agent rotenone or 6-hydroxydopamine (6-OHDA) were quantitatively analyzed for α-synuclein or TNF-α by PCR and immunoblotting.

Figure 30:
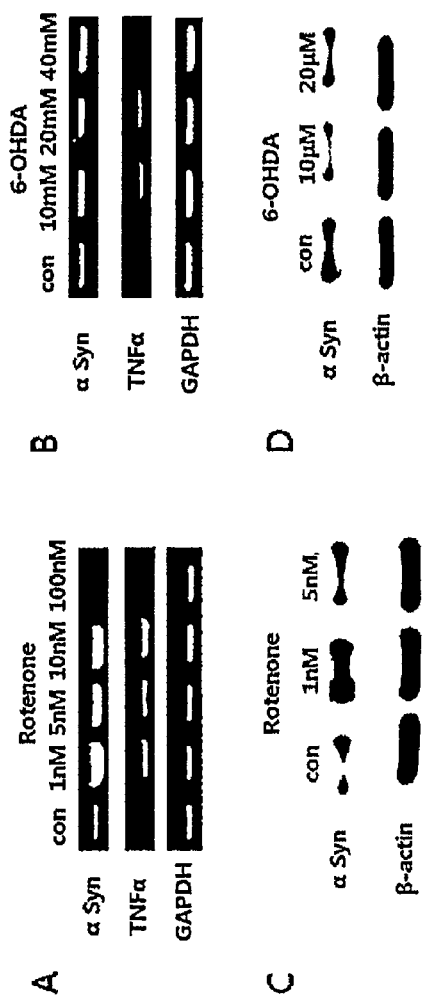
FIG. 30 shows expression levels of α-synuclein and TNF-α in human microglial cells after exposure to the Parkinson's disease causing agent rotenone or 6-hydroxydopamine (6-OHDA), as measured by PCR (A, B) and immunoblotting (C, D).

The results are given in FIG. 30.

As can be seen in FIG. 30, the Parkinson's disease causing agent rotenone or 6-hydroxydopamine increased the expression level of α-synuclein or TNF-α in human microglial cells, so that the human microglial cells were activated.

EXAMPLE 17

Synthesis and Secretion of AGE-Albumin in Human Microglial Cell Model of Parkinson's Disease An examination was made of the synthesis and secretion of AGE-albumin in human microglial cells exposed to 0~100 nM rotenone. In this regard, cell lysates and cell culture media were analyzed for AGE-albumin using ELISA and immunoblotting.

Figure 31:
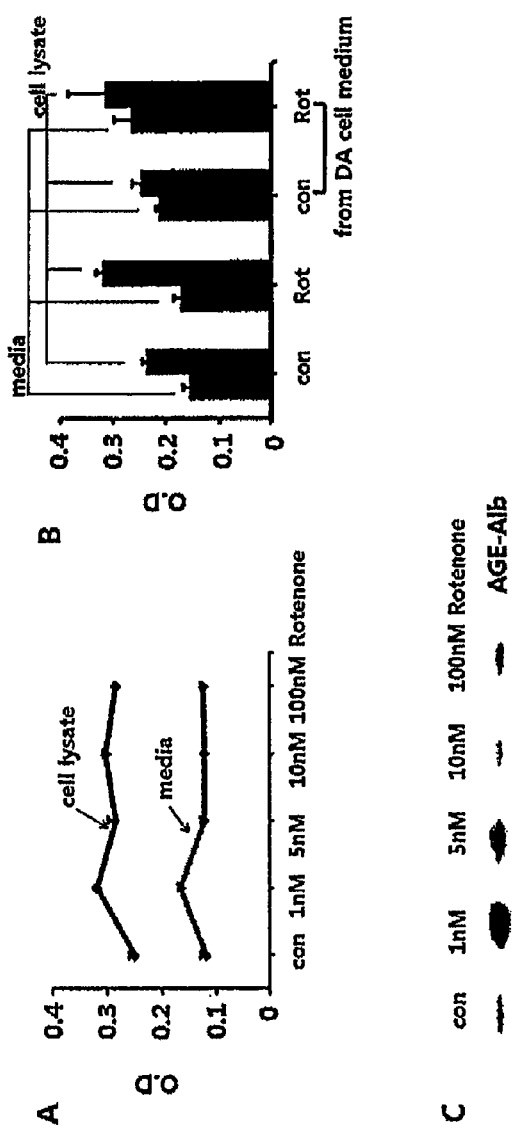
FIG. 31 shows the synthesis and secretion of AGE-albumin in human microglial cells exposed to 0~100 nM rotenone, as analyzed by ELISA and immunoblotting using cell lysates and cell culture media.

The results are given in FIG. 31.

An increased expression level of AGE-albumin in both cell lysate and cell culture medium was detected at 1 nM rotenone, as shown in FIG. 23.

EXAMPLE 18

Increased Synthesis and Secretion of α-Synuclein or AGE-Albumin by Oxidative Stress in Human Microglial Cell Model of Parkinson's Disease In order to examine whether the synthesis and secretion of a-synuclein or AGE-albumin in the human microglial cell model of Parkinson's disease is directly induced by oxidative stress, the human microglial cells were exposed to the Parkinson's disease causing agent rotenone and then to 0~1000 μM hydrogen peroxide ($H_2O_2$), an inducer of oxidative stress, followed by immunoblot analysis with cell lysates. Also, an immunoblot analysis was performed to examine whether the synthesis and secretion of α-synuclein or AGE-albumin in the human microglial cell model of stroke is directly reduced by the α-synuclein inhibitor cytochalasin D or the antioxidant ascorbic acid.

Figure 32:
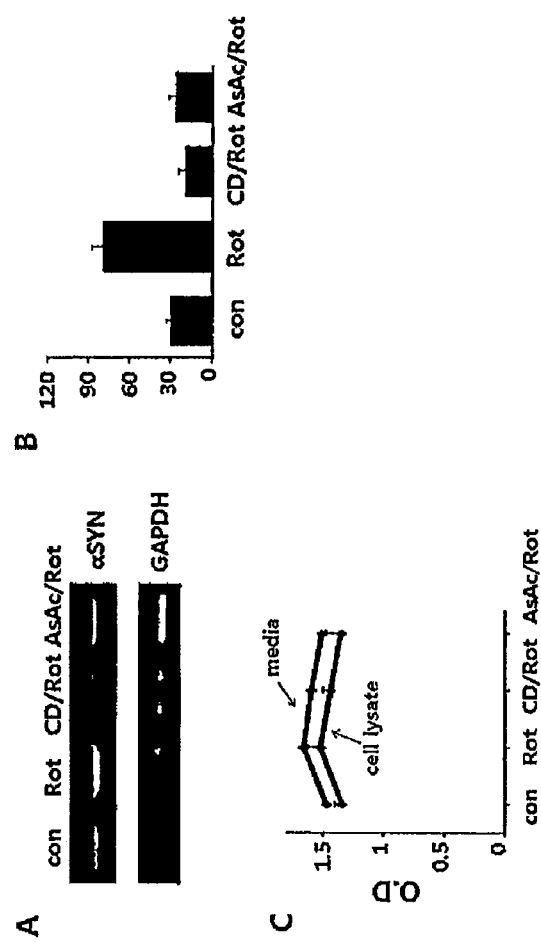
FIG. 32 shows the expression levels of α-synuclein and AGE-albumin in the human microglial cells exposed to rotenone under oxidative stress, as analyzed by immunoblotting.

The result is given in FIG. 32.

As is apparent from the data of FIG. 32, when the human microglial cells were sequentially exposed to rotenone and hydrogen peroxide ($H_2O_2$), amounts of both α-synuclein and AGE-albumin were increased in a concentration-dependent manner. In contrast, the addition of the α-synuclein inhibitor cytochalasin D or the antioxidant ascorbic acid drastically reduced the expression level of AGE-albumin irrespective of rotenone treatment.

EXAMPLE 19

Induction of Neuronal Cell Death by AGE-Albumin in Dopamine Neuronal Cells

Experiments were carried out to examine whether AGE-albumin induce neuronal death in dopamine neuronal cells, as follows.

1. Culture of Dopamine Neuronal Cells

Dopamine neuronal cells were grown in DMEM (Gibco, 10% FBS (Gibco), 0.1% gentamicin (Gibco), a high concentration of glucose) at 37° C. in a 5% $CO_2$ incubator. The cultured cells were incubated for 24 hrs with AGE-albumin (Sigma, 10 μg/mL) before use in the following experiments.

2. Immunohistochemistry and Immunoblotting

To examine whether AGE-albumin directly activates the MAPK signaling pathway and upregulates Bax in the dopamine neuronal cells from human brain tissues, cell lysates from dopamine neuronal cells treated with or without AGE-albumin before or after sRAGE exposure were analyzed for the expression levels of RAGE, Bax, SAPK/JNK, pSAPK/JNK, p38, ERK1/2, and pERK1/2 by immunoblotting. In addition, to examine the protective effect of soluble RAGE (sRAGE) on neuronal cells against cell death, absorbance at 540 nm was read.

Figure 33:
FIG. 33 shows expression levels of RAGE, Bax, SAPK/JNK, pSAPK/JNK, p38, ERK1/2, and pERK1/2 in cell lysates from dopamine neuronal cells treated with or without AGE-albumin treated before and after exposure to sRAGE, as measured by immunoblotting.

The results are given in FIG. 33.

As can be seen in FIG. 33, the level of RAGE was significantly increased after the dopamine neuronal cells were exposed to AGE-albumin in the absence of sRAGE. Also, significant increases were observed in the levels of SAPK/JNK and pSAPK/JNK, but not pERK1/2, p38, and pp38, by AGE-albumin, thus activating MAPK and Bax, a pro-apoptotic protein. In addition, expression levels of RAGE, SAPK/JNK, pSAPK/JNK, and Bax in dopamine neuronal cells exposed to sRAGE and then to AGE-albumin were comparable with the control, thus demonstrating that sRAGE is protective against neural death.

EXAMPLE 20

Protection by Soluble RAGE (sRAGE) Against Rotenone-Mediated Neuronal Death: In Vivo Assay To investigate the protective effect of sRAGE against rotenone-mediated neuronal death, an in vivo assay was performed after injection of rotenone alone or co-injection of rotenone/sRAGE into rat brains.

1. Animal Model

CBL57/bL6 mice, each weighing 20-25 g, were used as experimental animals. The mice were maintained on a 12-h light-dark cycle, allowed to have access to food and water ad libitum, and acclimated for at least 1 week prior to usage. All animal experiments were approved by the Institute Animal Care and Use Committee, and were conducted humanely.

Oral administration of rotenone for one month caused Parkinson's disease in mice. The animal models of Parkinson's disease were anaesthetized with ketamine (0.75 mg/kg body weight) and rompun (0.2 mg/kg body weight) prior to surgical procedures. For in vivo treatments, phosphate buffered saline (PBS) and sRAGE (10 ng/μL) were dissolved at a concentration of 1 mM in sterile water and kept at 4° C. until use. The head was fixed on a stereotaxic instrument before a midline incision of the scalp skin was made. The skull was pierced with a biological electric drill at the bregma (posteriorly, 0.3 mm; laterally, 2 mm) and the needle (gauge 26) on a 10-μL Hamilton syringe was lowered vertically until it reached the target area (depth, 2.5 mm). Three microliters of sRAGE were injected slowly at the rate of 1 μL per minute with an automatic microinjector. Thereafter, the syringe was removed slowly and surgical wounds were sutured with wound clips followed by topical treatment with antibiotics. For control, PBS was injected into the entorhinal cortex of normal mice.

Most mice were bred for one week and one month after injection of sRAGE. During the breeding, oral administration of rotenone still continued. Afterwards, all mice were re-anaesthetized in the same manner, and perfused transcardially with 100~200 mL of heparinized saline at 18° C. followed by 400 mL of 4% paraformaldehyde-lysine periodate in 0.1 M sodium phosphate buffer (pH, 7.4). The brains were removed, placed in the same fixative for 4 hrs at 4° C., and then transferred into ice-cold 0.1 M phosphate-buffered saline (PBS) containing 20% sucrose. The brains were cut in a transverse plane at 10 μm thickness with a freezing microtome and were stored at −80° C. until use.

2. Number of Neuronal Cells in Mouse Brain Tissues

The relative levels of neurons in mouse brain tissues were evaluated by cresyl violet staining after PBS, rotenone, or rotenone/sRAGE administration for one week and one month before microscopy.

Figure 34:
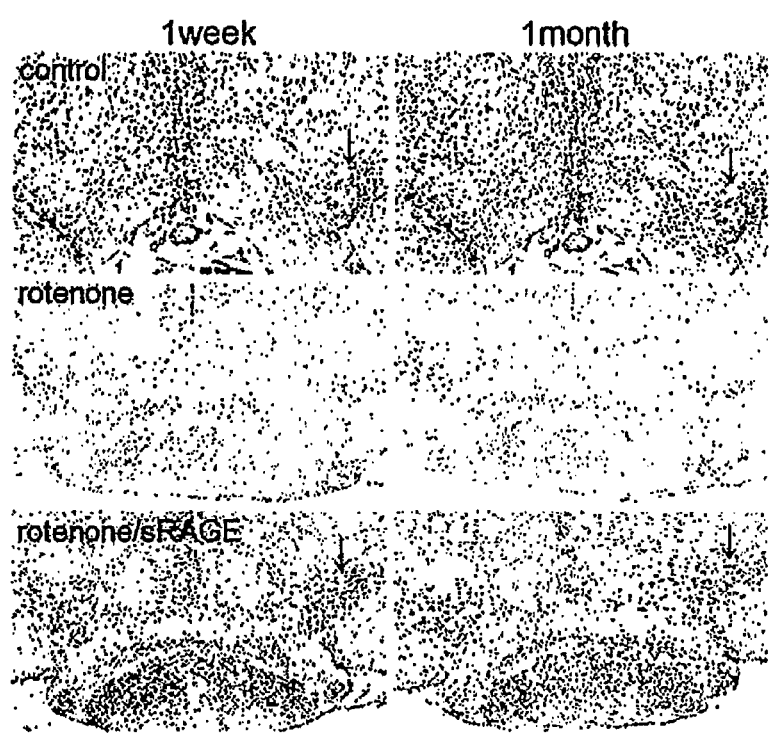
FIG. 34 shows microphotographs taken from mouse brain tissues stained with cresyl violet one week and one month after exposure to PBS, rotenone, or rotenone/sRAGEA in which the relative levels of neurons are determined.

The results are given in FIG. 34.

As seen in FIG. 34, a higher degree of cell death was observed in the brain tissues of the mice treated with rotenone, compared to non-treated mice. In addition, the treatment of mouse brain tissues with rotenone/sRAGE showed a significantly reduced level of cell death, and revived a significant number of neuronal cells, compared to PBS. Particularly, a higher number of neurons was observed in the region injected with sRAGE (arrow, right) than the non-injected region (arrow, left), with a predominant recovery in the substantia nigra.

3. Distribution and Localization of AGE-Albumin in Mouse Brain Tissue

Mouse brain tissues were treated with PBS, rotenone, or rotenone/sRAGE for one week and one month, and immunostained with labels for AGE-albumin, RAGE, and Bax, followed by laser confocal fluorescence microscopy to determine the distribution and localization of AGE-albumin, RAGE, and Bax.

Figure 35:
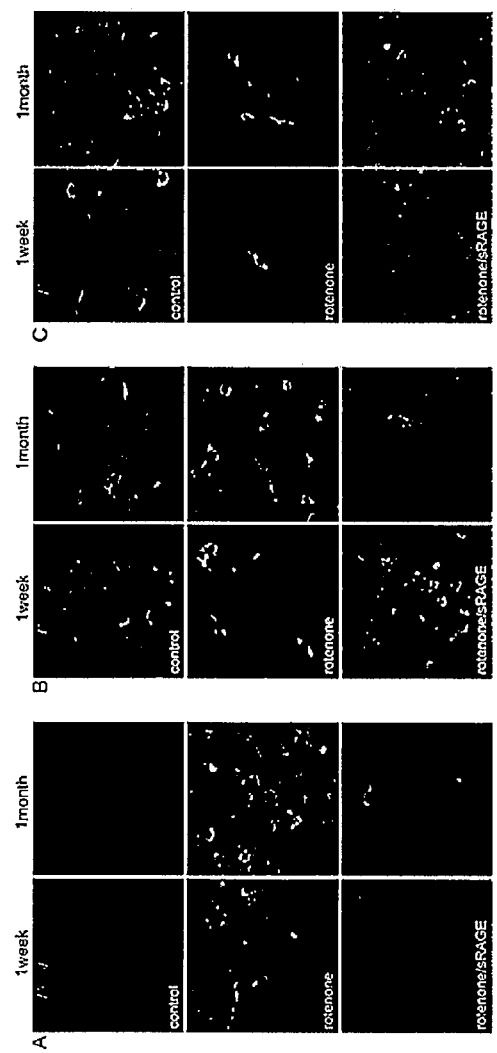
FIG. 35 shows laser confocal fluorescence microphotographs taken from mouse brain tissues in which distributions and localizations of AGE-albumin RAGE, and Bax in mouse brain tissues are represented by fluoroimmunostaining one week and one month after treatment with PBS, rotenone, or rotenone/sRAGEA.

The results are given in FIG. 35.

As can be seen in FIG. 35, the relative numbers of AGE, albumin, and Iba1 (microglial cells) AGE-albumin, RAGE, and Bax positive cells were increased in rotenone-administered mouse brains, but decreased in rotenone/sRAGE-administered rat brains.

EXAMPLE 21

Synthesis and Secretion of AGE-Albumin in Macrophage Model of Rheumatoid Arthritis β2-Microglobulin is abundantly found in the cartilage of rheumatoid arthritis patients. However, the precise role of β2-microglobulin synthesis in the cartilage and the correlation between β2-microglobulin and host macrophages or chontrocytes have remained unknown thus far. Accordingly, experiments were carried out to examine the effect of β2-microglobulin on macrophage activity and whether β2-microglobulin induces the synthesis of TNF-α and IL-β in macrophages.

1. Cell Culture and Construction of Cell Model of Arthritis

Macrophages (U937) from human lymphoma were cultured in RPMI 1640 (Thermo, 10% FBS (Gibco), 0.1% gentamicin (Gibco), a high concentration of glucose) at 37° C. in a 5% $CO_2$ incubator. Then, the human macrophages (U937) were exposed to β2-microglobulin (Sigma, 50 μg/mL) for 24 hrs to prepare a cell model of arthritis.

2. Expression of TNF-α, IL-1β, and AGE-Albumin in Macrophage Model of Rheumatoid Arthritis Human macrophages (U937) were treated with β2-microglobulin (0 μg, 12.5 μg, 25 μg, 50 μg), after which cell lysates and cell culture media were analyzed for the expression levels of TNF-α and IL-1β and for the synthesis and secretion of AGE-albumin using immunoblotting and ELISA.

Figure 36:
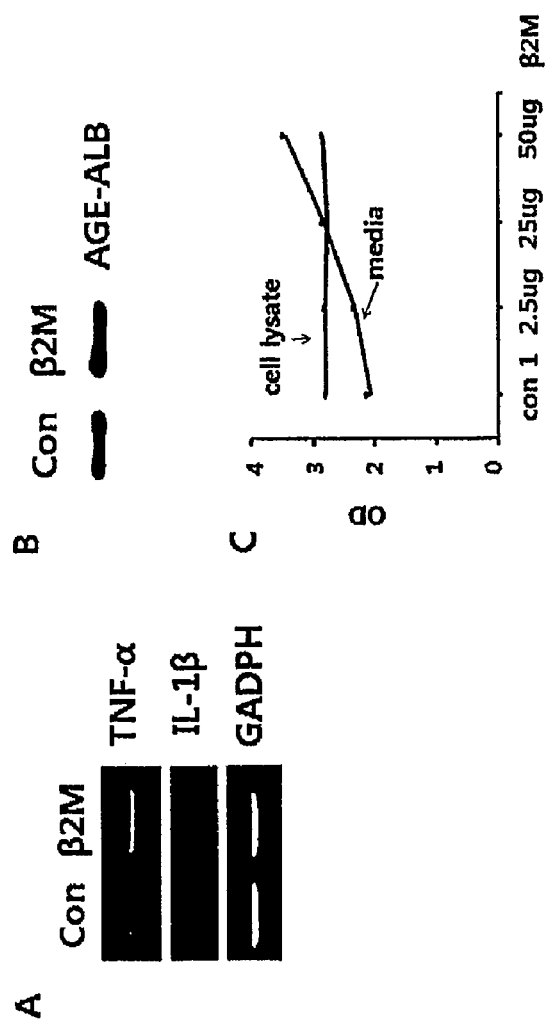
FIG. 36 shows the expression levels of TNF-α and IL-β, and the synthesis and secretion of AGE-albumin, as measured by immunoblotting and ELISA using cell lysates and cell culture media obtained from the culture of human macrophages (U937) treated with β2-microglobulin.

The results are given in FIG. 36.

Increased expression levels of TNF-α, IL-1β and AGE-albumin AGE-albumin in both cell lysate and cell culture medium were detected after human macrophages (U937) were treated with β2-microglobulin, and the secreted level of AGE-albumin was increased in a concentration-dependent manner.

EXAMPLE 22

Induction of Cell Death by AGE-Albumin in Chondrocytes

The following experiments were carried out to examine whether AGE-albumin induces chondrocytes to undergo apoptosis.

1. Culture of Chondrocytes

Human chondrocytes were grown at 37° C. in a chondrocyte growth medium (Promo Cell) supplemented with SupplementMix (Promo Cell) in a 5% $CO_2$ incubator.

2. Cell Viability (MTT Assay)

The cultured chondrocytes were seeded at a density of $2\times10^3$ cells/well into 96-well plates. When reaching 80% confluence, the chondrocytes were treated with AGE-albumin (Sigma, 10 μg/mL). After 24 hours of treatment, the cells were rinsed with PBS and examined for viability using an MTT [3-(4,5-dimethylthiazol-2-yl)-2,5-diphenyl tetrazolium bromide] assay. Absorbance in each well was read at 540 nm.

Figure 37:
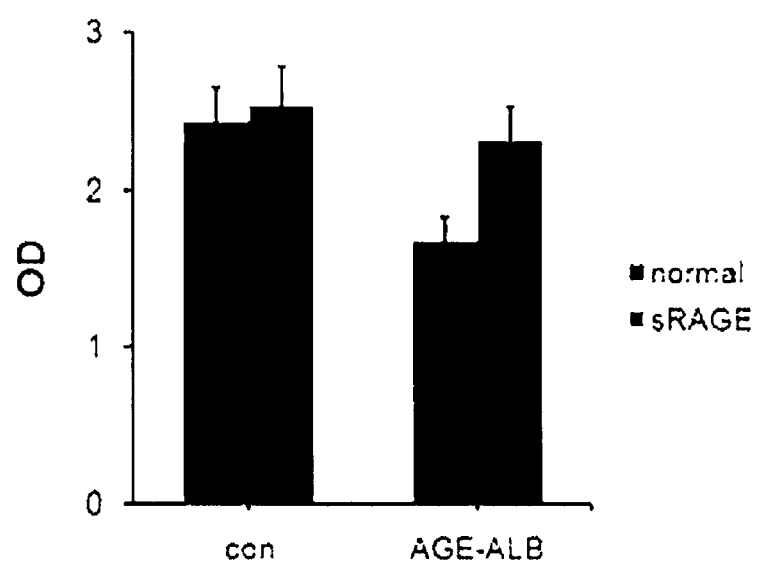
FIG. 37 is a graph showing the cell viability of chontrocytes exposed to AGE-albumin alone or in combination with sRAGE, as measured by MTT assay.

The results are given in FIG. 37.

When chondrocytes were treated with AGE-albumin, as seen in FIG. 37, the cell viability decreased with an increase in AGE-albumin concentration, indicating that AGE-albumin induces cell death. In contrast, when chondrocytes were co-treated with sRAGE and AGE-albumin, the cell viability was comparable with the control, indicating that sRAGE can protect chondrocytes from cell death.

EXAMPLE 23

Selection of Candidates for Inhibitor of AGE-Albumin Synthesis

Candidates for inhibitors of AGE-albumin synthesis in human microglial cells were selected from among LOPAC (Sigma) compounds as follows.

1. Selection of Inhibitors of AGE-Albumin Synthesis in Human Microglial Cell Model of Alzheimer's Disease Human microglial cells were seeded at a density of $1\times10^4$ cells/200 μL into 96-well microplates and maintained for 24 hrs. The cells were incubated with 2 μM Aβ1-42 (Sigma) for 6 hrs and then with 1280 LOPAC (Sigma, 5 μM) compounds for 24 hrs. After completion of incubation, the cells were fixed in 100% ethanol and reacted with an AGE-albumin antibody (1:10,000, Abcam) and then with a peroxidase-conjugated secondary antibody (1:5000, Vector). Color was developed with TMB (Sigma) followed by measuring absorbance at 450 nm on an ELISA reader. Selection was made of candidates for an inhibitor of AGE-albumin synthesis.

Of the 1280 LOPAC compounds, a total of 42 were selected as candidates for an inhibitor of AGE-albumin synthesis in a human microglial cell model of Alzheimer's disease. The selected candidates are summarized in Table 1, below. ELISA results of the candidates are shown in FIG. 38.

TABLE 1

| No. | Cpd. Name |
|---|---|
| C-1 | Amantadine hydrochloride |
| C-2 | Gabaculine hydrochloride |
| C-3 | YM 976 |
| C-4 | Acetyl-beta-methylcholine chloride |
| C-5 | 5-Aminovaleric acid hydrochloride |
| C-6 | p-Aminoclonidine hydrochloride |
| C-7 | Azelaic acid |
| C-8 | 4-Amino-1,8-naphthalimide |
| C-9 | (+)-Butaclamol hydrochloride |
| C-10 | Acetohexamide |
| C-11 | Paroxetine hydrochloride hemihydrates (MW = 374.83) |
| C-12 | cis-4-Aminocrotonic acid |
| C-13 | Aniracetam |
| C-14 | HEMADO |
| C-15 | Psora-4 |
| C-16 | Gamma-Acetylinic GABA |
| C-17 | S(−)-Atenolol |
| C-18 | (±)-Baclofen |
| C-19 | Bupropion hydrochloride |
| C-20 | Cefaclor |
| C-21 | Cephalothin sodium |
| C-22 | Debrisoquin sulfate |
| C-23 | Phenytoin sodium |
| C-24 | N6-Cyclohexyladenosine |
| C-25 | CK2 Inhibitor 2 |
| C-26 | 1,4-Dideoxy-1,4-imino-D-arabinitol |
| C-27 | N-Methyl-1-deoxynojirimycin |
| C-28 | 2,4-Dinitrophenyl 2-fluoro-2-deoxy-beta-D-glucopyranoside |
| C-29 | SANT-1 |
| C-30 | Clodronic acid |
| C-31 | Emetine dihydrochloride hydrate |
| C-32 | Edrophonium chloride |
| C-33 | Ellipticine |
| C-34 | Furafylline |
| C-35 | Fluoxetine hydrochloride |
| C-36 | Glybenclamide |
| C-37 | GW2974 |
| C-38 | 3-Isobutyl-1-methylxanthine |
| C-39 | Leflunomide |
| C-40 | 4-Methylpyrazole hydrochloride |
| C-41 | BIO |
| C-42 | Mifepristone |

Figure 38:
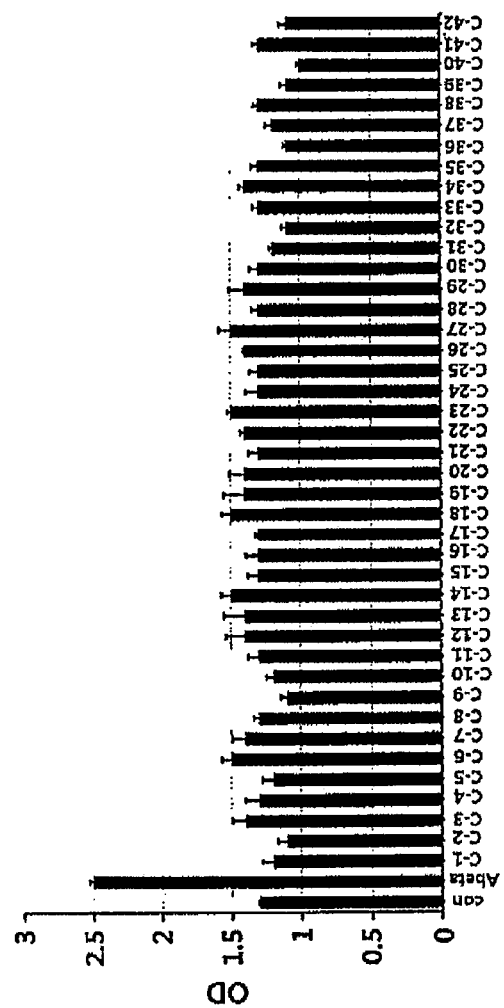
FIG. 38 is a graph showing ELISA results of candidates, selected from among 1280 LOPAC compounds, for inhibitors of AGE-albumin synthesis in a human microglial cell model of Alzheimer's disease.

As seen in FIG. 38, the candidates for inhibitors of AGE-albumin synthesis in a human microglial cell model of Alzheimer's disease had similar inhibitory activity against the synthesis of AGE-albumin to that of the control.

2. Selection of Inhibitors of AGE-Albumin in Human Microglial Cell Model of Parkinson's Disease Human microglial cells were plated at a density of $1 \times 10^4$ cells/200 μL/well into 96-well plates and grown for 24 hrs. The cells were treated for 24 hrs with a culture medium used to grow dopamine neuronal cells for 10 days in the presence of rotenone (Sigma 1 nM), and then exposed for 24 hrs to 1280 LOPAC (Sigma) compounds (5 μM). Thereafter, the cells were fixed in 100% methanol, and reacted with a primary AGE-albumin antibody (1:10000, Abcam) and then with a peroxidase-conjugated secondary antibody (1:5000, Vector). Color was developed with TMB (Sigma) before absorbance at 450 nm was measured using an ELISA reader. Selection was made of candidates for an inhibitor of AGE-albumin synthesis.

Of the 1280 LOPAC compounds, a total of 9 were selected as candidates for an inhibitor of AGE-albumin synthesis in a human microglial cell model of Alzheimer's disease. The selected candidates are summarized in Table 2, below. ELISA results of the candidates are shown in FIG. 39.

TABLE 2

| No. | Cpd. Name |
|---|---|
| C-11 | Paroxetine hydrochloride hemihydrate (MW = 374.83) |
| C-12 | cis-4-Aminocrotonic acid |
| C-17 | S(−)-Atenolol |
| C-18 | (±)-Baclofen |
| C-19 | Bupropion hydrochloride |
| C-20 | Cefaclor |
| C-21 | Cephalothin sodium |
| C-26 | 1,4-Dideoxy-1,4-imino-D-arabinitol |
| C-27 | N-Methyl-1-deoxynojirimycin |

Figure 39:
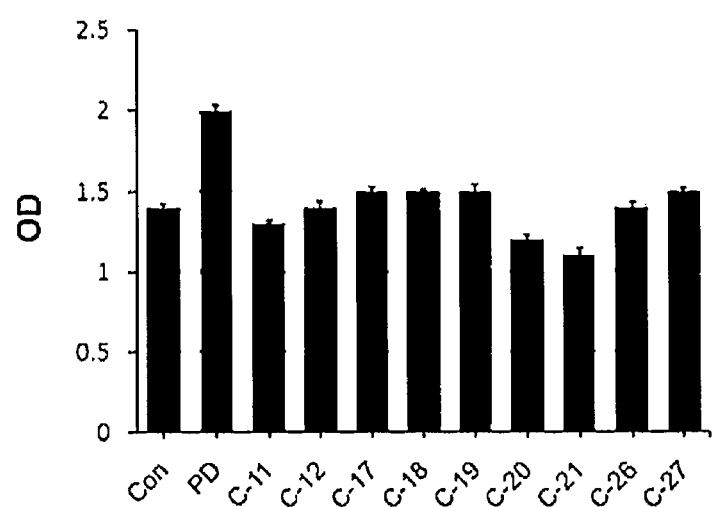
FIG. 39 is a graph showing ELISA results of inhibitors of AGE-albumin synthesis in a human microglial cell model of Alzheimer's disease, selected from among the candidates.

As can be seen in FIG. 39, the candidates for inhibitors of AGE-albumin synthesis in a human microglial cell model of Alzheimer's disease had similar inhibitory activity against the synthesis of AGE-albumin to that of the control.

EXAMPLE 24

Effect of Inhibitors of AGE-Albumin Synthesis on Rotenone-Mediated Neuronal Cell Death To examine the effect of inhibitors of AGE-albumin synthesis on rotenone-mediated neuronal cell death, C-20 (Cefaclor) and C-21 (Cephalothin sodium), among the inhibitors of AGE-albumin synthesis selected in Example 23, were injected into mouse brain tissues, after which the same procedure as in Example 20 was repeated to observe the number of neuronal cells, and the distribution and localization of AGE-albumin, RAGE, and Bax in mouse brain tissues.

Figure 40:
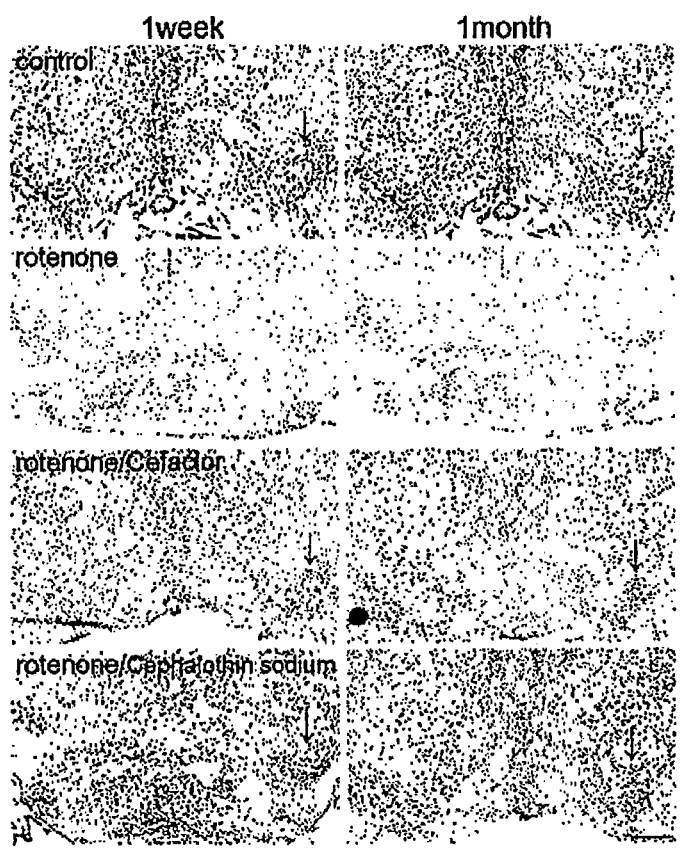
FIG. 40 shows microphotographs taken from mouse brain tissues stained with cresyl violet one week and one month after exposure to PBS, rotenone, rotenone/Cefaclor, or rotenone/Cephalothin sodium in which the relative levels of neurons are determined.

The relative levels of neurons in mouse brain tissues were evaluated by cresyl violet staining after treatment with PBS, rotenone, rotenone/Cefaclor, and rotenone/Cephalothin sodium for one week and one month before microscopy. The results are shown in FIG. 40. On the other hand, the distribution and localization of AGE-albumin, RAGE, and Bax in mouse brain tissues were evaluated by fluoroimmunostaining after treatment PBS, rotenone, rotenone/Cefaclor, and rotenone/Cephalothin sodium for one week and one month before confocal fluorescence microscopy. The results are given in FIG. 41.

As seen in FIG. 40, a higher degree of cell death was observed in the brain tissues of the mice treated with rotenone, compared to non-treated mice. In addition, the treatment of mouse brain tissues with rotenone/Cefaclor or rotenone/Cephalothin sodium showed a significantly reduced level of cell death, and revived a significant number of neuronal cells, compared to PBS. Particularly, a higher number of neurons was observed in the region injected with Cefaclor or Cephalothin sodium (arrows, right) than the non-injected region (arrows, left), with a predominant recovery in the substantia nigra. Higher efficiency was obtained in Cephalothin sodium than Cefaclor.

Figure 41:
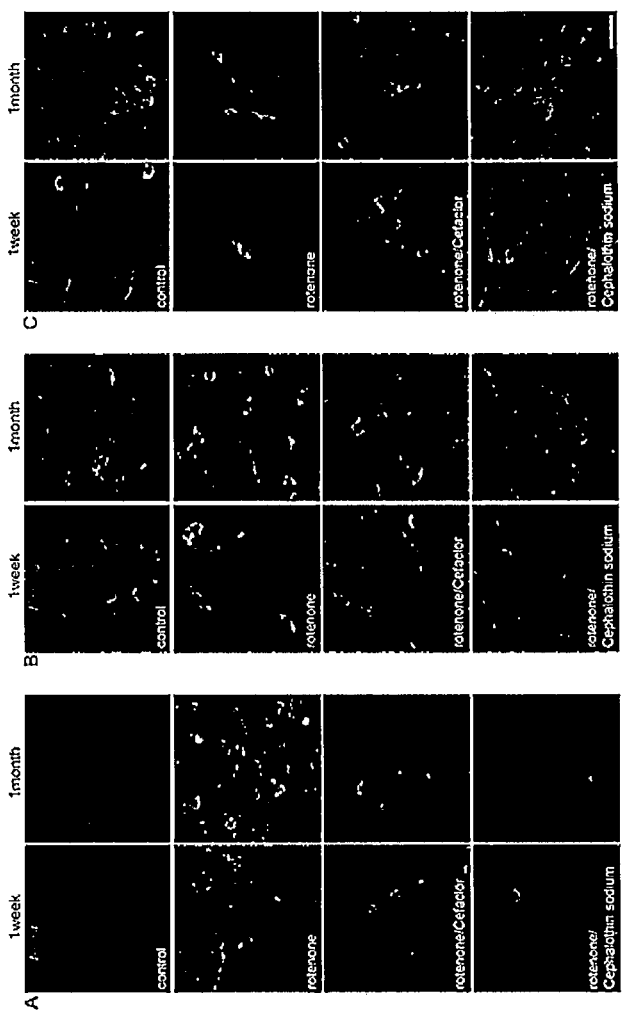
FIG. 41 shows laser confocal fluorescence microphotographs taken from mouse brain tissues stained with labels for AGE-albumin, RAGE, and Bax one week and one month after exposure to PBS, rotenone, rotenone/Cefaclor, or rotenone/Cephalothin sodium in which distributions and localizations of AGE-albumin, RAGE, and Bax are determined.

In addition, as can be seen in FIG. 41, expression levels of AGE, albumin, the microglial marker Iba1, AGE-albumin, RAGE, and Bax were increased in the brain tissues of the mice orally administered with rotenone, but were reduced in the brain tissues of the mice orally administered with rotenone/Cefaclor, or rotenone/Cephalothin sodium.

Formulation examples are given to illustrate dosage preparations containing the composition of the present invention.

FORMULATION EXAMPLE 1

Preparation of Powder

Inhibitor of AGE-albumin synthesis 0.1 g
Lactose 1.5 g
Talc 0.5 g
These ingredients were mixed and loaded into an airtight sac to provide a powder.

FORMULATION EXAMPLE 2

Preparation of Tablet

Inhibitor of AGE-albumin synthesis 0.1 g
Lactose 7.9 g
Crystalline cellulose 1.5 g
Magnesium stearate 0.5 g
These ingredients were mixed and directly compressed into a tablet.

FORMULATION EXAMPLE 3

Preparation of Capsule

Inhibitor AGE-albumin synthesis 0.1 g
Corn starch 5 g
Carboxycellulose 4.9 g
These ingredients were admixed together and the admixture was loaded into a conventional capsule using a suitable device.

FORMULATION EXAMPLE 4

Preparation of Injection

Inhibitor AGE-albumin synthesis 0.02~0.2 g
Sterile water for injection suitable amount
pH Adjuster suitable amount
Stabilizer suitable amount
Using a conventional method, these ingredients were put into an ampule (2 ml) to give an injection.

FORMULATION EXAMPLE 5

Preparation of Liquid Medicine

Inhibitor AGE-albumin synthesis 0.1 g
Isomerized sugar 10 g
Mannitol 5 g
Purified water suitable amount
Each ingredient was dissolved in purified water and flavored with lemon before admixing together. Purified water was added to the admixture to form a final volume of 100 ml which was then loaded into a brown vial and sterilized.

The invention claimed is:

1. A method for inhibiting induction of cell death, comprising administering to a subject an agent that inhibits the synthesis or secretion of advanced glycation-endproduct (AGE)-albumin, wherein the inhibition of induction of cell death is accomplished by inhibiting the synthesis or secretion of AGE-albumin in a cell of a mononuclear phagocyte system, and wherein the agent is selected from the group consisting of the following compounds C-3 to C-7, C-12, C-14, C-24, C-26, C-28 to C-31, C-34, C-37, and C-38:

| No. | Compound Name |
|---|---|
| C-3 | YM 976 (4-(3-Chlorophenyl)-1,7-diethylpyrido[2,3-d]pyrimidin-2-one) |
| C-4 | Acetyl-beta-methylcholine chloride |
| C-5 | 5-Aminovaleric acid hydrochloride |
| C-6 | p-Aminoclonidine hydrochloride |
| C-7 | Azelaic acid |
| C-12 | cis-4-Aminocrotonic acid |
| C-14 | HEMADO (2-(1-Hexynyl)-N-methyladenosine) |
| C-24 | N6-Cyclohexyladenosine |
| C-26 | 1,4-Dideoxy-1,4-imino-D-arabinitol |
| C-28 | 2,4-Dinitrophenyl 2-fluoro-2-deoxy-beta-D-glucopyranoside |
| C-29 | SANT-1 ((E)-N-(4-Benzylpiperazin-1-yl)-1-(3,5-dimethyl-1-phenylpyrazol-4-yl)methanimine) |
| C-30 | Clodronic acid |
| C-31 | Emetine dihydrochloride hydrate |
| C-34 | Furafylline |
| C-37 | GW2974 (4-N-(1-benzylindazol-5-yl)-6-N,6-N-dimethylpyrido[3,4-d]pyrimidine-4,6-diamine) |
| C-38 | 3-Isobutyl-1-methylxanthine. |

2. The method of claim 1, wherein the cell of which death is inhibited is a cell around the cell of a mononuclear phagocyte system.

3. The method of claim 2, wherein the cell around the cell of a mononuclear phagocyte system is selected from the group consisting of a neuronal cell, a chondrocyte, a pneumocyte, a hepatocyte, and a combination thereof.

4. The method of claim 1, wherein the synthesis or secretion of AGE-albumin is inhibited using at least one selected from the group consisting of an albumin siRNA, an albumin antibody, an AGE antibody, an AGE-albumin antibody, and an inhibitor of AGE-albumin synthesis.

5. The method of claim 1, wherein the cell of the mononuclear phagocyte system is selected from the group consisting of a brain microglial cell, a blood monocyte, an alveolar macrophage (type II pneumocyte, dust cell), a peritoneal macrophage, a granuloma macrophage in an inflammation region, a splenic macrophage, a Kupffer's cell of a liver, a synovial A cell, an adventitial cell, a macrophage within a lymph node, and an epidermal Langerhans cell.

6. The method of claim 4, wherein the synthesis or secretion of AGE-albumin is inhibited using an inhibitor of AGE-albumin synthesis.

* * * * *